United States Patent
Shinno et al.

(10) Patent No.: US 7,085,343 B2
(45) Date of Patent: Aug. 1, 2006

(54) X-RAY COMPUTED TOMOGRAPHY APPARATUS

(75) Inventors: Toshiyuki Shinno, Otawara (JP); Yuji Yanagida, Otawara (JP); Shigeyuki Nakashima, Yaita (JP); Yoshiaki Yaoi, Nasu-gun (JP); Miwa Okumura, Kuroiso (JP); Minoru Horinouchi, Otawara (JP); Masahiko Yamazaki, Shioya-gun (JP); Machiko Iso, Nasu-gun (JP); Satoru Nakanishi, Utsunomiya (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 243 days.

(21) Appl. No.: 10/272,014

(22) Filed: Oct. 17, 2002

(65) Prior Publication Data

US 2003/0076920 A1    Apr. 24, 2003

(30) Foreign Application Priority Data

Oct. 18, 2001  (JP) .............................. 2001-320925
Oct. 18, 2001  (JP) .............................. 2001-320926
Oct. 18, 2001  (JP) .............................. 2001-320928
Oct. 18, 2001  (JP) .............................. 2001-320929

(51) Int. Cl.
*A61B 6/00* (2006.01)
*G01N 23/00* (2006.01)
*G21K 1/12* (2006.01)
*H05G 1/60* (2006.01)

(52) U.S. Cl. .............................. 378/9; 378/19; 378/92
(58) Field of Classification Search .................... 378/5, 378/9, 16, 19
See application file for complete search history.

(56) References Cited

U.S. PATENT DOCUMENTS

| | | | | |
|---|---|---|---|---|
| 4,032,789 A | * | 6/1977 | Workman | 378/14 |
| 4,672,651 A | * | 6/1987 | Horiba et al. | 378/62 |
| 5,459,769 A | * | 10/1995 | Brown | 378/4 |
| 5,485,493 A | * | 1/1996 | Heuscher et al. | 378/15 |
| 5,612,985 A | * | 3/1997 | Toki et al. | 378/4 |
| 6,198,790 B1 | * | 3/2001 | Pflaum | 378/9 |
| 6,208,706 B1 | * | 3/2001 | Campbell et al. | 378/9 |
| 6,256,369 B1 | * | 7/2001 | Lai | 378/14 |
| 6,404,844 B1 | * | 6/2002 | Horiuchi et al. | 378/8 |
| 6,760,399 B1 | * | 7/2004 | Malamud | 378/9 |
| 2004/0114706 A1 | * | 6/2004 | Ikeda et al. | 378/4 |

OTHER PUBLICATIONS

U.S. Appl. No. 10/272,014, filed Oct. 17, 2002, Shinno et al.
U.S. Appl. No. 10/640,355, filed Aug. 14, 2003, Ozaki.

* cited by examiner

*Primary Examiner*—Craig E. Church
*Assistant Examiner*—Thomas R. Artman
(74) *Attorney, Agent, or Firm*—Oblon, Spivak, McClelland, Maier & Neustadt, P.C.

(57) ABSTRACT

An X-ray computed tomography apparatus of this invention includes a first data detecting system which includes a first X-ray tube and a first X-ray detector and a second data detecting system which includes a second X-ray tube and a second X-ray detector. A reconstructing unit reconstructs image data on the basis of the data detected by at least one of the first and second data detecting systems. A monitoring unit monitors the first data detecting system. In a period during which the first data detecting system is normal, data acquisition is performed by both the first and second data detecting systems. In a period during which the first data detecting system is faulty, data acquisition is performed by the second data detecting system alone.

19 Claims, 26 Drawing Sheets

$\Delta d (= S1/2 + S2/2)$

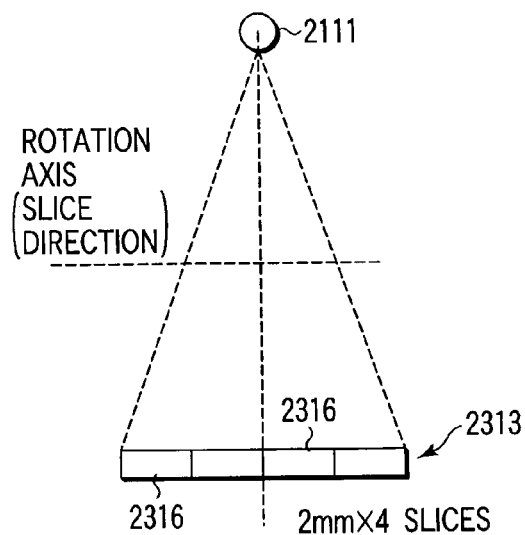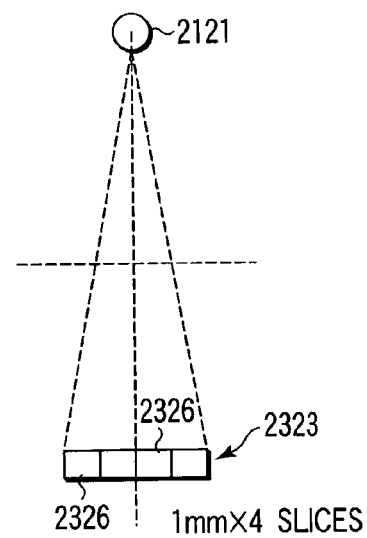
FIG. 16A    FIG. 16B
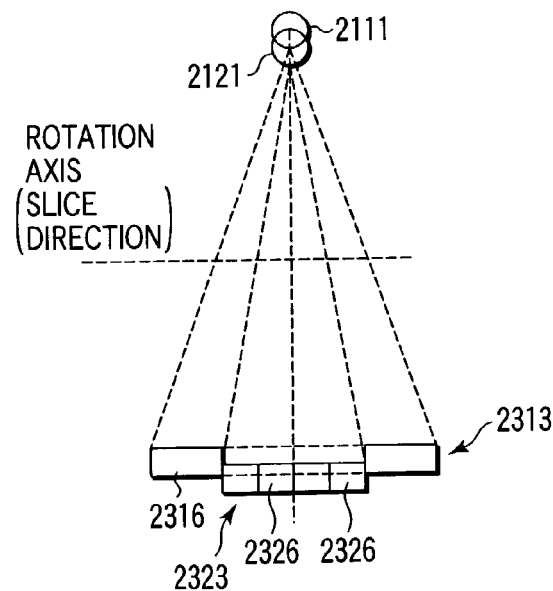
FIG. 17

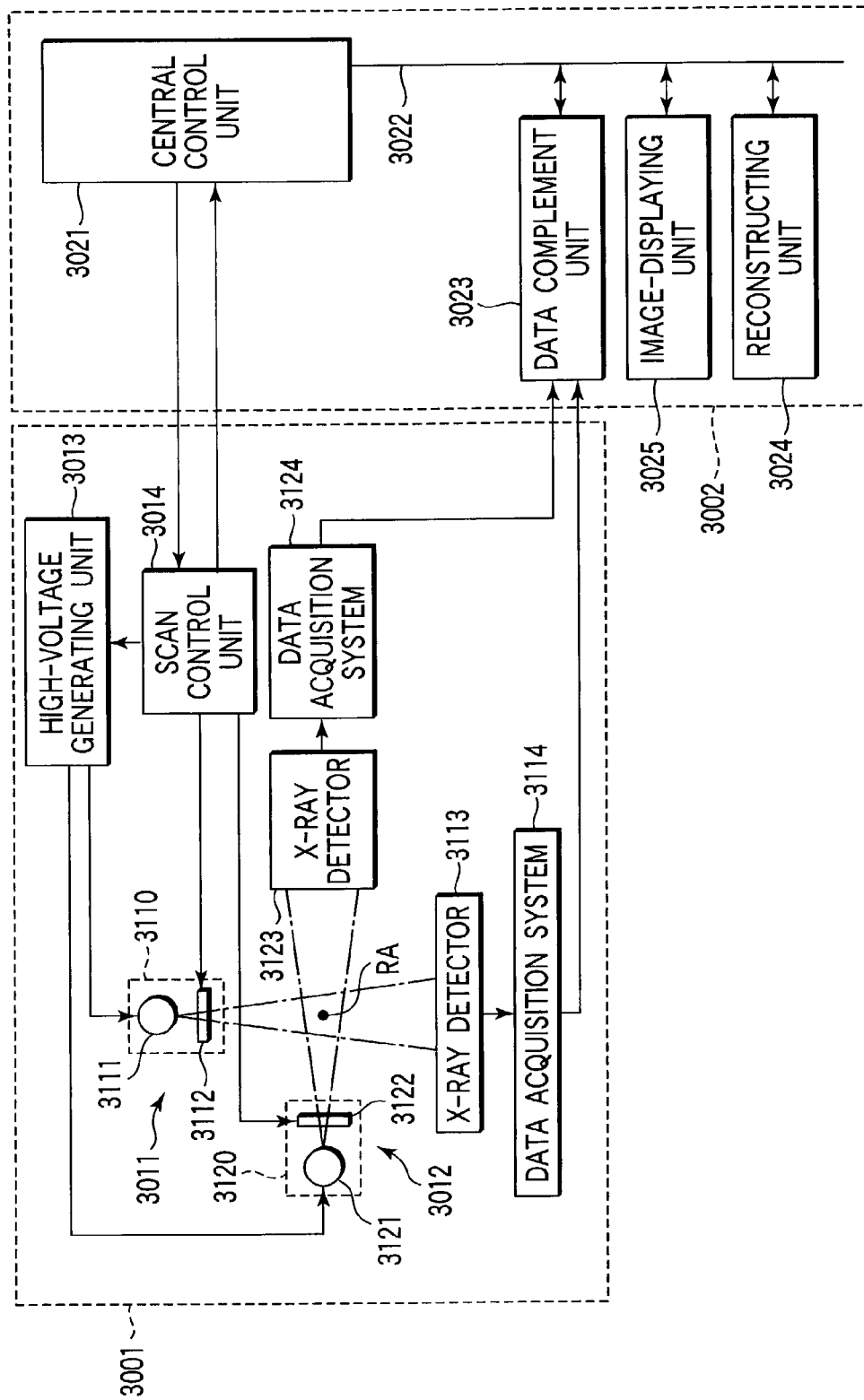
F I G. 18

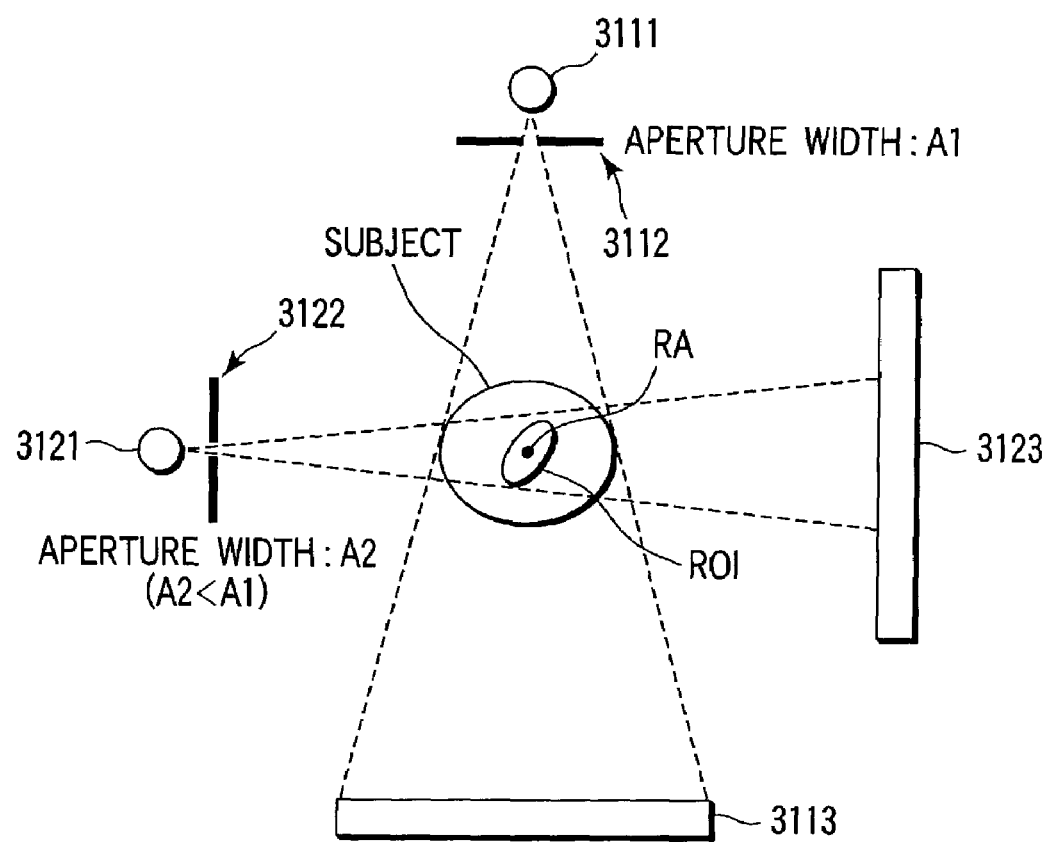
F I G. 19

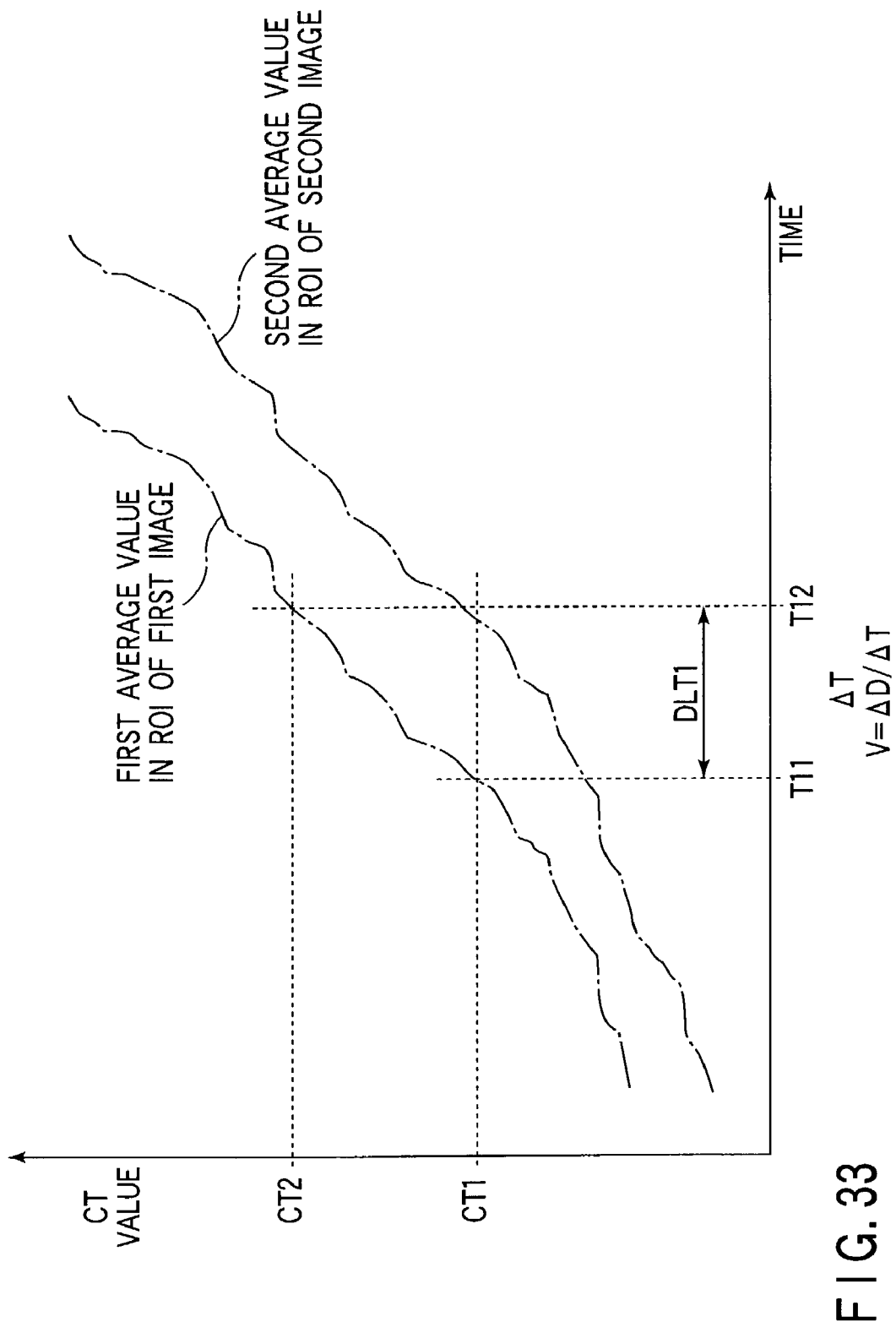
F I G. 33

X-RAY COMPUTED TOMOGRAPHY APPARATUS

CROSS-REFERENCE TO RELATED APPLICATIONS

This application is based upon and claims the benefit of priority from the prior Japanese Patent Applications No. 2001-320925, filed Oct. 18, 2001; No. 2001-320926, filed Oct. 18, 2001; No. 2001-320928, filed Oct. 18, 2001; No. 2001-320929, filed Oct. 18, 2001, the entire contents of all of which are incorporated herein by reference.

BACKGROUND OF THE INVENTION

1. Field of the Invention

The present invention relates to an X-ray computed tomography apparatus having the function of monitoring abnormal operation such as abnormal discharge or the like in an X-ray tube unit.

2. Description of the Related Art

As is known, a helical scan by which projection data in a wide region of a subject to be examined can be continuously and seamlessly acquired at a high speed is realized by synchronous motions, i.e., the continuous rotation of an X-ray tube, a multi-channel type X-ray detector, and the like and the movement of the table-top of a bed on which the subject is placed.

Most of the currently available X-ray computed tomography apparatuses are equipped with an interlock function of monitoring the state of an X-ray tube on the basis of a tube voltage, a tube current, a filament heating current, an intra-tube temperature, the operation state of a cool pump, and the like and stopping scan operation including X-ray irradiation as needed.

Conventionally, when this interlock function is activated to stop X-ray irradiation, the cause is sought and solved. In addition, if the operator gives no error clear instruction, the overall scan operation including X-ray irradiation is stopped.

Such an interlock function is very convenient and an indispensable function in improving safety. On the other hand, a scan must often be started all over again. In a contrast medium examination or the like, for example, a change in CT value over time is one of the most important information. If a scan is stopped halfway by the interlock function, the contrast enhancement effect is almost lost. For this reason, a contrast medium must be injected again to redo a scan from the beginning. In the above helical scan, even if the scan operation is resumed from the scan stop time, discontinuous data may be obtained due to a change in the posture of a subject to be examined or the like during the time the scan is stopped. In such a case as well, a scan must be redone from the beginning.

In general, an X-ray tube is equipped with a diaphragm device and designed to change the slice thickness by adjusting the aperture width of the diaphragm. Since the slice thickness is determined depending on a diaphragm aperture width, it is determined before data acquisition, and there is basically no degree of freedom in changing the slice thickness after data acquisition. If, therefore, tomographic images having different slice thicknesses are required, the operator must repeat a scan upon changing the diaphragm aperture width. Jpn. Pat. Appln. KOKAI Publication No. 9-215688 discloses a technique of simultaneously acquiring data having different slice thicknesses by using a dual detector. However, data are obtained at different slice positions (different slice center positions). When, therefore, tomographic images having different slice thicknesses are required at the same slice position, a scan must also be repeated.

Recently, a semiconductor detector which directly converts X-rays transmitted through a subject to be examined into electric charges has been developed, and the X-ray irradiation dose, i.e., the exposure dose, tends to decrease with an improvement in the sensitivity of the detector. However, the reduction in exposure dose has its limit. As the exposure dose becomes a predetermined amount or less, the density resolution considerably decreases, resulting in incapability of ensuring image quality suitable for diagnosis.

In contrast-medium imaging, it is important to perform a scan (a helical scan in this case; a monitor-scan is discriminated from a main-scan) at the timing a contrast medium injected into a subject to be examined flows into an imaging region. For this reason, the flow of the contrast medium must be monitored at a position upstream of the imaging region. That is, a scan is consecutively repeated at a monitoring position, and tomographic image data is reconstructed and displayed in real time from the resultant projection data.

The operator observes this tomographic image and inputs a trigger for a main-scan at the timing the degree of staining of a blood vessel of interest increases to a certain extent. Upon reception of this trigger, the apparatus stops the monitor-scan and moves the table-top to a scan start position in the imaging region. In addition, the apparatus waits for setups of scan conditions (X-ray emission conditions, helical pitch, and the like) for a main-scan from the operator, switches the output voltages of the high voltage generating unit in accordance with the setup conditions, and pre-heats the filament. After this preparation is completed, the apparatus actually starts a main-scan by giving a tube voltage and trigger. As described above, table-top movement, setups, and emission preparation are required before a main-scan is actually started.

The time required for these operations is not short. For this reason, a main-scan may start with a delay with respect to the proper timing a contrast medium begins to flow into an imaging region. In order to prevent such a situation, a trigger for a main-scan must be input at the timing when the degree of staining of a blood vessel is not very high, in consideration of the operation time. This timing determination requires expert knowledge and experience.

BRIEF SUMMARY OF THE INVENTION

It is an object of the present invention to allow an X-ray computed tomography apparatus to continue a scan even if an abnormal situation occurs.

It is another object of the present invention to allow an X-ray computed tomography apparatus to acquire data about slices having different slice thicknesses at the same slice position in one scan.

It is still another object of the present invention to reduce the exposure dose and ensure high image quality at the same time in an X-ray computed tomography apparatus.

It is still another object of the present invention to reduce a deviation from the main-scan start timing by shortening the time required for a shift from a monitor-scan in which a contrast medium is injected to a main-scan.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; a reconstructing unit which reconstructs image data on the basis of the data detected by at least one of the first and second data detecting systems; a monitoring unit which monitors the first data detecting system; and a scan control unit which controls scan operation such that data acquisition is performed by both the first and second data detecting systems in a period during which the first data detecting system is normal, and data acquisition is performed by the second data detecting system alone in a period during which the first data detecting system is faulty.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; a monitoring unit which monitors the first data detecting system; and a reconstructing unit which reconstructs image data on the basis of the data acquired by both the first and second data detecting systems in a period during which the first data detecting system is normal, and reconstructs image data on the basis of the data acquired by the second data detecting system in a period during which the first data detecting system is faulty.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; a reconstructing unit which reconstructs image data on the basis of the data detected by at least one of the first and second data detecting systems; a monitoring unit which monitors the first data detecting system; and a scan control unit which controls scan operation such that data acquisition is performed by the first data detecting system in a period during which the first data detecting system is normal, and data acquisition is performed by the second data detecting system in a period during which the first data detecting system is faulty.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; a reconstructing unit which reconstructs image data on the basis of the data detected by at least one of the first and second data detecting systems; a monitoring unit which monitors the first data detecting system; and a scan control unit which controls scan operation such that data acquisition is performed by the first data detecting system in a period during which the first data detecting system is normal, and the data acquisition is continued by switching from the first data detecting system to the second data detecting system in a period during which the first data detecting system is faulty.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; a monitoring unit which monitors the first data detecting system; and a reconstructing unit which reconstructs image data on the basis of the data acquired by the first data detecting system in a period during which the first data detecting system is normal, and reconstructs image data on the basis of the data acquired by the second data detecting system in a period during which the first data detecting system is faulty.

According to the first aspect of the present invention, there is provided an X-ray computed tomography apparatus comprising: a first data detecting system which includes a first X-ray tube and a first X-ray detector; a second data detecting system which includes a second X-ray tube and a second X-ray detector; and a reconstructing unit which reconstructs first image data corresponding to a first slice thickness on the basis of an output from the first X-ray detector, and reconstructs second image data corresponding to a second slice thickness smaller than the first slice thickness on the basis of output from the second X-ray detector.

According to the first aspect of the present invention, there is provided an X-ray computed tomography apparatus comprising: a first detecting system configured to have a first X-ray tube which irradiates a subject to be examined with X-rays, a first X-ray collimator which limits a divergence angle of X-rays from the first X-ray tube and can change an aperture width, and a first X-ray detector which detects X-rays emitted from the first X-ray tube and transmitted through the subject; a second detecting system configured to have a second X-ray tube which irradiates a subject to be examined with X-rays, a second X-ray collimator which limits a divergence angle of X-rays from the second X-ray tube and can change an aperture width, and a second X-ray detector which detects X-rays emitted from the second X-ray tube and transmitted through the subject; a scan control unit configured to set the aperture width of the second X-ray collimator to be lower than the aperture width of the first X-ray collimator; and a reconstructing unit configured to reconstruct image data on the basis of projection data obtained by the first X-ray detector and projection data obtained by the second X-ray detector.

According to the first aspect of the present invention, there is provided an X-ray computed tomography apparatus comprising: a plurality of detecting systems each configured to have an X-ray tube which irradiates a subject to be examined with X-rays, an X-ray collimator which limits a divergence angle of X-rays from the X-ray tube and can change an aperture width, and an X-ray detector which detects X-rays emitted from the X-ray tube and transmitted through the subject; a scan control unit configured to set an aperture width of the X-ray collimator of at least one the plurality of data detecting systems to be smaller than an aperture width of the X-ray collimators of the remaining data detecting systems; and a reconstructing unit configured to reconstruct image data on the basis of projection data obtained by the plurality of X-ray detectors.

According to the first aspect of the present invention, there is provided an X-ray computed tomography apparatus comprising: a plurality of detecting systems each configured to have an X-ray tube which irradiates a subject to be examined with X-rays, an X-ray collimator which limits a divergence angle of X-rays from the X-ray tube and can change an aperture width, and an X-ray detector which detects X-rays emitted from the X-ray tube and transmitted through the subject, the X-ray collimator of at least one of the plurality of data detecting systems having an aperture width smaller than that of the X-ray collimators of the remaining data detecting systems; and a reconstructing unit configured to reconstruct image data on the basis of projection data obtained by the plurality of X-ray detectors.

According to the first aspect of the present invention, there is provided an X-ray computed tomography apparatus comprising: a plurality of detecting systems each configured to have an X-ray tube which irradiates a subject to be examined with X-rays, an X-ray collimator which limits a divergence angle of X-rays from the X-ray tube and can change an aperture width, and an X-ray detector which detects X-rays emitted from the X-ray tube and transmitted through the subject, the aperture widths of the plurality of X-ray collimators being capable of being set independently; and a reconstructing unit configured to reconstruct image data on the basis of projection data obtained by the plurality of X-ray detectors.

According to the first aspect of the present invention, there is provided an X-ray computed tomography apparatus comprising: a first detecting system which has a first X-ray tube which irradiates a subject to be examined with X-rays at a first irradiation dose, and a first X-ray detector which detects X-rays transmitted through the subject; a second detecting system which has a second X-ray tube which irradiates the subject with X-rays at a second irradiation dose higher than first irradiation dose, and a second X-ray detector which detects X-rays transmitted through the subject; and a moving mechanism configured to move at least one of the first and second data detecting systems in a body axis direction of the subject.

According to the first aspect of the present invention, there is provided an X-ray computed tomography apparatus comprising: a plurality of data detecting systems each of which has an X-ray tube which irradiates a subject to be examined with X-rays and an X-ray detector which detects X-rays transmitted through the subject; a reconstructing unit configured to reconstruct image data in real time on the basis of an output from the detector of at least one of the plurality of data detecting systems; and a control unit configured to monitor a flow of a contrast medium into a main-scan region, which is injected into the subject, on the basis of the image data, and make another data detecting system of the plurality of data detecting systems start data acquisition when the contrast medium flows into the main-scan region.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 16A and 16B are views showing the slice thicknesses of the first and second data detecting systems in another modification of this embodiment;

FIG. 17 is a view showing the positions of the first and second data detecting systems in FIGS. 16A and 16B;

FIG. 18 is a block diagram showing the arrangement of the main part of an X-ray computed tomography apparatus according to the third embodiment of the present invention;

FIG. 19 is a view showing the aperture widths of the first and second collimators in FIG. 18;

FIG. 33 is a graph for explaining a method of calculating a delay time DLT1 between a monitor-scan stop to a main-scan start in the fourth control operation in FIG. 32B, showing changes in the average values of CT values in the first and second data detecting systems over time.

DETAILED DESCRIPTION OF THE INVENTION

Figure 1:
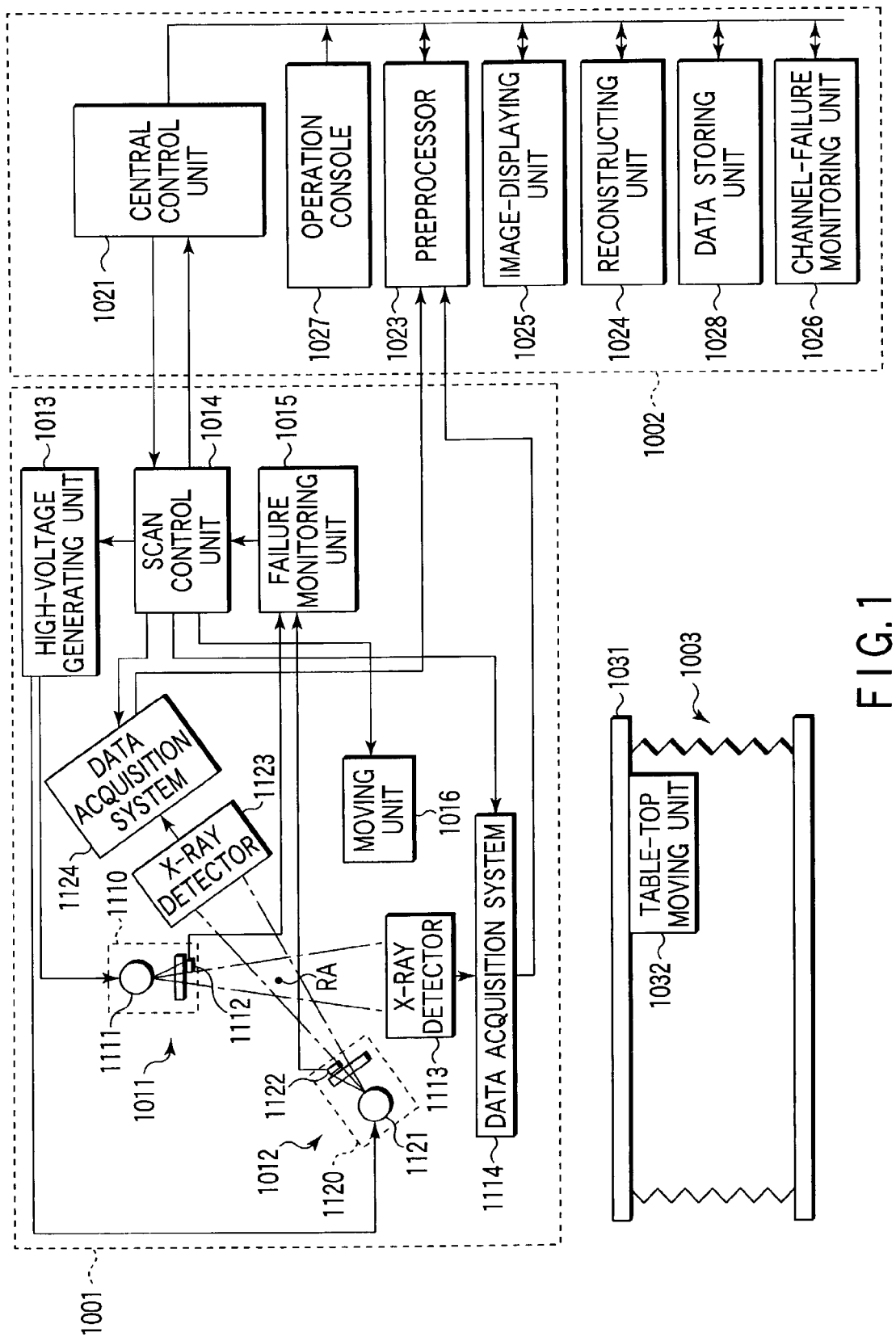
FIG. 1 is a block diagram showing the main part of an X-ray computed tomography apparatus according to the first embodiment of the present invention.

X-ray computed tomography apparatuses according to the preferred embodiments of the present invention will be described in more detail below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements arrayed in the form of a ring are fixed, and only an X-ray tube rotates around a subject to be examined. The present invention can be applied to either type. In this case, the rotate/rotate type, which is currently the mainstream, will be exemplified.

In order to reconstruct one-slice tomographic image data, one projection data set of about 360° corresponding to one rotation around a subject to be examined is required, or one set of 210° to 240° projection data is required in the half scan method. The present invention can be applied to either of these schemes. In this case, the former scheme of reconstructing one tomographic image from a projection data set of about 360°, which is a general scheme, will be exemplified.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified.

A tomographic image is a slice display of a tissue having a certain thickness; the thickness of the tissue slice is termed a slick thickness. X-rays radially diverge from the focal point of the X-ray tube, pass through a subject to be examined, and reach the X-ray detector. Therefore, the thickness of X-rays increases with an increase in distance from the focal point of the X-ray tube. Conventionally, the thickness of X-rays on a rotational center axis is defined as a slice thickness. According to convention, in this case, the thickness of X-rays on the rotational center axis is termed a slice thickness. This applies to the width of a detection element in the slice direction. In the expression "a detection element having a sensitivity width corresponding to a certain slice thickness", the sensitivity width is actually larger than the slice thickness. More specifically, this sensitivity width is designed to be larger than the slice thickness in accordance with the ratio of the distance between the X-ray focal point and the rotational center axis to the distance between the X-ray focal point and the detection element.

(First Embodiment)

FIG. 1 shows the arrangement of the main part of an X-ray computed tomography apparatus according to this embodiment. The X-ray computed tomography apparatus according to the embodiment is comprised of a scan gantry 1001, computer device 1002, and bed 1003. The scan gantry 1001 is a constituent element for acquiring projection data about a subject to be examined. This projection data is loaded into the computer device 1002 and subjected to processing such as image reconstruction. The subject is inserted into the imaging area of the scan gantry 1001 while lying on the table-top of the bed. The bed 1003 is equipped with a table-top moving unit 1032 for electrically moving a table-top 1031 along its longitudinal axis (almost equivalent to the body axis of the subject laid on the bed). The computer device 1002 is comprised of a central control unit 1021, a preprocessor 1023 connected to the central control unit 1021 via a data/control bus 1022, an operation console 1027, a data storing unit 1028, a reconstructing unit 1024, an image displaying unit 1025, and a channel failure monitoring unit 1026.

Figure 2:
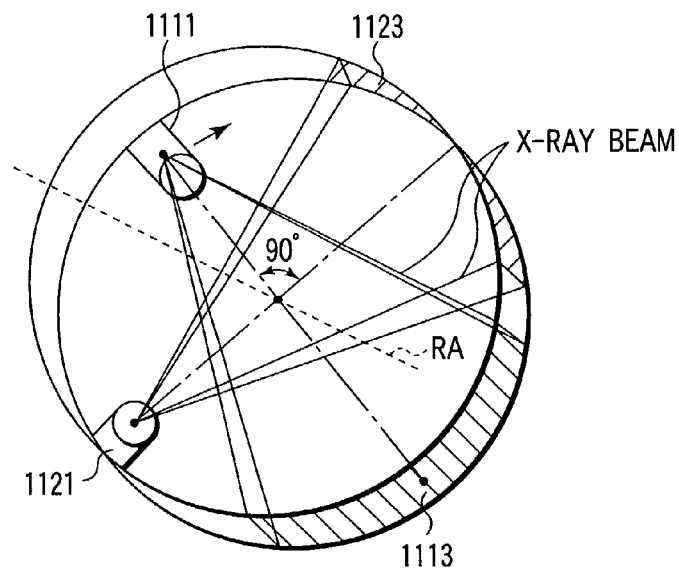
FIG. 2 is a perspective view showing the arrangement of the first and second detectors in FIG. 1.

The scan gantry 1001 is of a multi-tube type, i.e., has a plurality of data detecting systems, each including an X-ray tube assembly and X-ray detector, mounted on an annular rotating gantry. In this case, the scan gantry 1001 will be described as a two-tube type gantry. As shown in FIG. 2, a first data detecting system 1011 has a first X-ray tube assembly 1110 and first X-ray detector 113 mounted on the rotating gantry. In a second data detecting system 1012, a second X-ray tube assembly 1120 and a second X-ray detector 1123 which faces it are mounted on the rotating gantry such that the central axis of the second data detecting system 1012 crosses the central axis of the first data detecting system 1011 at a rotation axis RA at a predetermined angle (assumed to be 90° herein). The rotating gantry on which the second data detecting system 1012 is mounted may be the same as that on which the first data detecting system 1011 is mounted or differ therefrom.

The second data detecting system 1012 is so supported by a moving unit 1016 as to be movable along the rotation axis RA. This makes it possible to set the position (to be referred to as the Z-position hereinafter) of the second data detecting system 1012 on the rotation axis RA at a position where it coincides with the Z-position of the first data detecting system 1011 or at a predetermined distance therefrom. In this embodiment, in a helical scan, the Z-position of the second data detecting system 1012 is shifted backward from the Z-position of the first data detecting system 1011 by a predetermined distance. In a single-slice scan, the Z-position of the second data detecting system 1012 is set at the same position or almost the same position as the Z-position of the first data detecting system 1011.

The first X-ray tube assembly 1110 is comprised of an X-ray tube 1111, a reference detector 1112, and peripheral elements (not shown) such as a cooling system, a filter, and a diaphragm. Likewise, the second X-ray tube assembly 1120 is comprised of an X-ray tube 1121, a reference detector 1122, and peripheral elements (not shown) such as a cooling system, a filter, and a diaphragm. The reference detectors 1112 and 1122 are disposed at positions where peripheral portions of X-rays are incident. A failure monitoring unit 1015 detects the operation states of the X-ray tubes 1111 and 1121, i.e., the occurrence of abnormal discharge (arc), from abrupt decreases in X-ray irradiation dose on the basis of outputs from the reference detectors 1112 and 1122 or variations in output therefrom. Note that the reference detectors 1112 and 1122 can be replaced with sensors based on other schemes. If tube current meters are used, the failure monitoring unit 1015 can detect the operation states of the X-ray tubes 1111 and 1121 from abrupt increases in tube current.

A high voltage generating unit 1013 applies tube voltages to the X-ray tube assemblies 1110 and 1120, supplies filament heating currents thereto, and controls the operations of the cooling systems, filters, diaphragms, and the like under the control of a scan control unit 1014. In addition to the control on the high voltage generating unit 1013, the scan control unit 1014 takes charge of all operation control required for a scan, including the rotation of the rotating gantry, the movement of the table-top 1031, changing of the Z-position of the second data detecting system 1012 by the moving unit 1016, and processing by data acquiring units 1114 and 1124, e.g., signal input/output operation and amplification/quantization.

The scan control unit 1014 is connected to the failure monitoring unit 1015. When the failure monitoring unit 1015 detects the occurrence of abnormal discharge in the X-ray tube 1111 or 1121, the scan control unit 1014 performs, with respect to the high voltage generating unit 1013, processing required to stop applying a tube voltage to the X-ray tube 1111 or 1121 in which the abnormal discharge has occurred and stop supplying a filament heating current. If the X-ray tube assemblies 1110 and 1120 are equipped with X-ray shutters, the shutters are closed at the same time as the application of tube voltages or independently thereof.

Assume that abnormal discharge has occurred. It is known that when tube voltage application is resumed after it is interrupted for a short period of time, normal operation often revives. The scan control unit 1014 has such an automatic revival function. That is, the scan control unit 1014 stops applying a tube voltage to the X-ray tube 1111 or 1121 in which a failure has occurred and also performs, with respect to the high voltage generating unit 1013, processing required to resume tube voltage application a predetermined period of time after the stop.

The data (termed raw data) acquired by the data acquiring units 1114 and 1124 are sent to the preprocessor 1023 of the computer device 1002 via a slip ring (not shown) that allows continuous rotation. The preprocessor 1023 corrects the raw data. The corrected raw data are in the stage immediately before reconstruction and termed projection data. The projection data are supplied to the data storing unit 1028 and stored therein. The reconstructing unit 1024 reconstructs tomographic image data on the basis of the projection data held in the data storing unit 1028. The addresses of the projection data read out from the data storing unit 1028 to the reconstructing unit 1024 for tomographic image reconstruction are managed by the central control unit 1021. In performing tomographic image reconstruction, the central control unit 1021 can arbitrarily switch a mode of using the data acquired by the first data detecting system 1011, a mode of using the data acquired by the second data detecting system 1012, and a mode of using the data acquired by the two systems in accordance with a predetermined rule.

Along with data acquisition, the channel failure monitoring unit 1026 monitors the occurrence of a channel failure on the basis of raw data or projection data. The channel failure monitoring unit 1026 compares data on adjacent channels of the detectors 1113 and 1123. If the difference in data value between the adjacent channels is larger than a predetermined threshold, the channel failure monitoring unit 1026 determines that a failure has occurred on one of the adjacent channels. It is easy to determine on which adjacent channel the failure has occurred. This is because both the difference in data value between the faulty channel and the adjacent channel on the right side and the difference in data value between the faulty channel and the adjacent channel on the left side are larger than the threshold.

When the number of channels of the plurality of channels constituting the detector 1113 on which failures have occurred exceeds a predetermined number, the channel failure monitoring unit 1026 determines that the detector 1113 is faulty and cannot be used. Likewise, when the number of channels of the plurality of channels constituting the detector 1123 on which failures have occurred exceeds the predetermined number, the channel failure monitoring unit 1026 determines that the detector 1123 is faulty and cannot be used. Upon determining that the detector 1113 or 1123 cannot be used, the channel failure monitoring unit 1026 supplies a signal corresponding to the determination to the central control unit 1021.

Upon receiving the signal indicating that the detector 1113 or 1123 cannot be used from the channel failure monitoring unit 1026, the central control unit 1021 supplies a signal corresponding to that the detector 1113 or 1123 cannot be used to the scan control unit 1014. Upon receiving the signal corresponding to that the detector 1113 or 1123 cannot be used, the scan control unit 1014 executes the same control operation as that to be done when an arc has occurred. The scan control unit 1014 performs, with respect to the high voltage generating unit 1013, processing required to stop applying a tube voltage to the X-ray tube 1111 or 1121 corresponding to the detector 1113 or 1123 which is determined not to be used and stop supplying a filament heating current thereto. If the X-ray tube assemblies 1110 and 1120 are equipped with X-ray shutters, the shutters are closed at the same time as the application of tube voltages or independently thereof.

Figure 3:
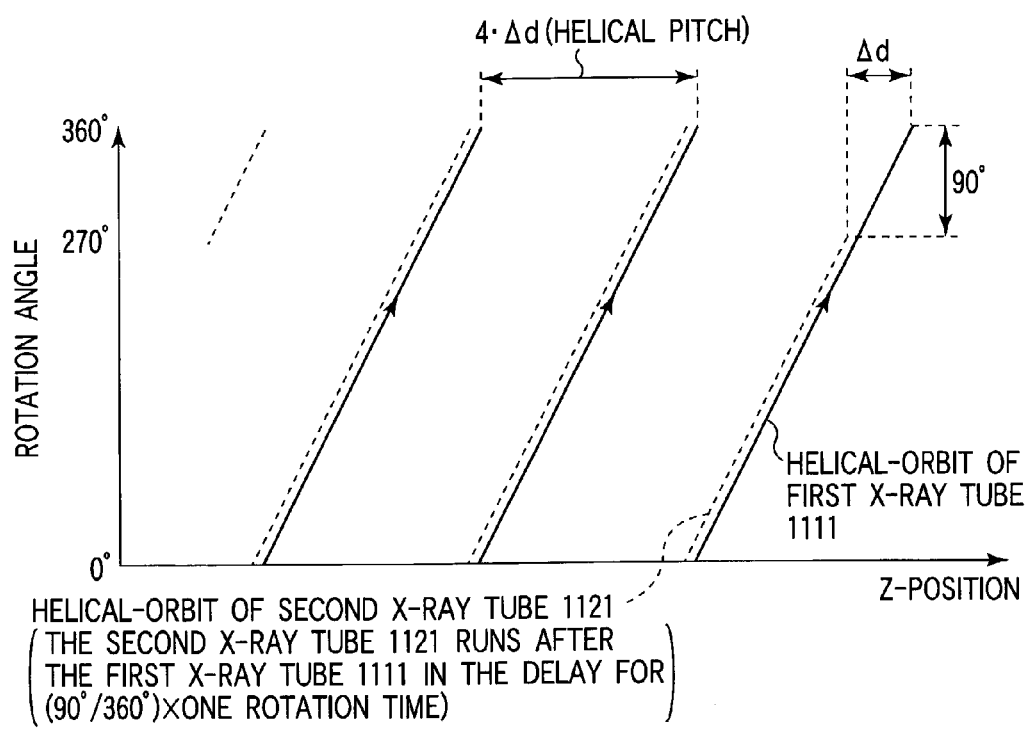
FIG. 3 is a graph showing the orbits of the first and second X-ray tubes in a helical scan according to this embodiment.

FIG. 3 shows the orbits of the first and second X-ray tubes 1111 and 1121 in a helical scan, with the ordinate and abscissa representing the rotation angle and Z-position, respectively. When a helical scan mode is designated, the moving unit 1016 sets the Z-position of the second data detecting system 1012 at a position shifted backward from the Z-position of the first data detecting system 1011 by a predetermined distance $\Delta d$. In addition, the rotation angle of the rotating gantry and the movement speed of the table-top 1031 are set on the basis of the shift distance $\Delta d$ under the control of the scan control unit 1014 such that the second X-ray tube 1121 follows the same or almost the same helical-orbit as that of the first X-ray tube 1111. More specifically, the above values are set such that a helical pitch defined as the movement distance of the table-top per rotation coincides with four times the shift distance $\Delta d$ (360°/shift angle (90° in this case)).

In this helical scan operation, while the first X-ray tube 1111 is normal, projection data are acquired by the first data detecting system 1011, and the second data detecting system 1012 rotates in a so-called idle state without acquiring any projection data. That is, in the period during which the first X-ray tube 1111 is normal, X-rays are actually emitted to the subject, and transmitted X-rays are detected by the first X-ray detector 1113. In this period, the subject is not irradiated with X-rays from the second X-ray tube 1121. The second X-ray tube 1121 may be inhibited from emitting X-rays by stopping the application of a tube voltage to the second X-ray tube 1121, blocking X-rays by the shutter, or another means. In the period during which the first X-ray tube 1111 is normal, the application of a tube voltage to the second X-ray tube 1121 is stopped, but a filament heating current is actually supplied to the second X-ray tube 1121. This is a technique of shortening the time lag between the instant at which a tube voltage begins to be applied to the second X-ray tube 1121 and the instant at which X-rays are actually emitted and the subject is irradiated with the X-rays.

Figure 4:
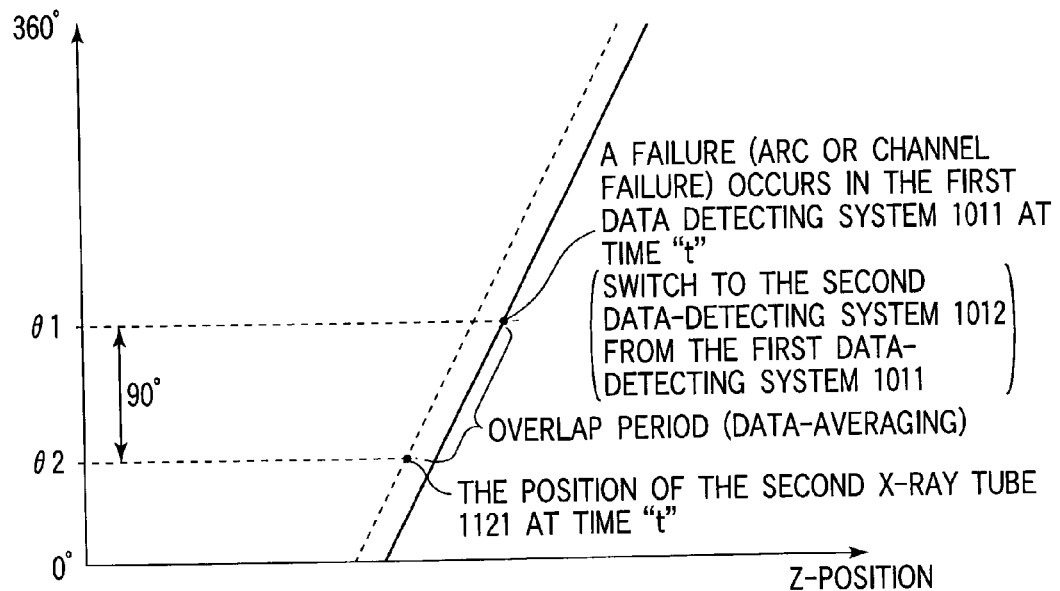
FIG. 4 is a graph for explaining a scan continuation function in a helical scan according to this embodiment.
Figure 5:
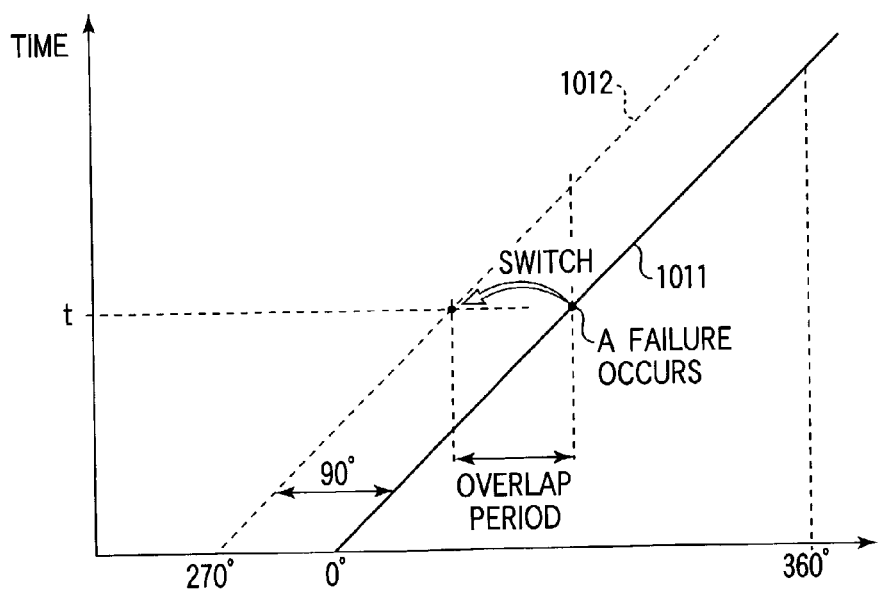
FIG. 5 is a graph for explaining in detail the scan continuation function in a helical scan according to this embodiment.

FIGS. 4 and 5 are graphs for explaining operation to be done when a failure such as abnormal discharge has occurred in the first X-ray tube 1111 or the first X-ray detector 1113 cannot be used because of the occurrence of a channel failure. FIGS. 4 and 5 should be referred to in consideration of the following points. Referring to FIG. 4, the ordinates represents the rotation angle; and abscissa, the Z-position. In contrast to this, referring to FIG. 5, the ordinates represents time; and the abscissa, the rotation angle.

A case wherein a failure such as abnormal discharge has occurred in the first X-ray tube 1111 will be described below. A case wherein the first X-ray detector 1113 cannot be used because of the occurrence of a channel failure is handled in the same manner as the case wherein a failure such as abnormal discharge has occurred in the first X-ray tube 1111.

Referring to FIGS. 4 and 5, a failure such as abnormal discharge has occurred in the first X-ray tube 1111 at time t. At time t, the first X-ray tube 1111 is located at a rotation angle θ1, and the second X-ray tube 1121 is located at a rotation angle θ2 which is 90° behind the rotation angle θ1. At time t, the scan control unit 1014 stops applying a tube voltage to the first X-ray tube 1111 and stops supplying a filament heating current thereto. At time t, the scan control unit 1014 starts applying a tube voltage to the second X-ray tube 1121 and also starts detection by the X-ray detector 1123 and data acquisition by the data acquisition system 1124.

Since data acquisition is switched from the first data detecting system 1011 to the second data detecting system 1012 in this manner at the time of the occurrence of a failure, even if data acquisition is stopped in the first data detecting system 1011 due to the occurrence of the failure, the second data detecting system 1012 takes over the operation. This makes it possible to continue the helical scan.

With regard to tomographic image reconstruction, a tomographic image is reconstructed from the data acquired by the first data detecting system 1011 in a scan cycle before time t when the failure has occurred. A scan cycle is defined as a cycle in which the X-ray tube 1111 rotates, from a reference position (a 0° position in general; a displacement occurs periodically (180°+fan angle α) at a time), through an angle range (360° or 180°+α) required to reconstruct one tomographic image.

Tomographic image reconstruction processing may be performed concurrently with the helical scan to realize so-called CT fluoroscopy, or may be non-real-time processing that is started after the helical scan.

In the scan cycle including failure occurrence time t, a tomographic image is reconstructed by preparing projection data corresponding to an angle (360° or 180°+α (fan angle)) necessary for the reconstruction of one tomographic image from the data acquired by the first data detecting system 1011 before the occurrence of the failure and the data acquired by the second data detecting system 1012 after the occurrence of the failure. Note that since the second data detecting system 1012 moves with a predetermined time delay with respect to the first data detecting system 1011, data corresponding to 90° immediately before time t are redundantly acquired by the first data detecting system 1011 and second data detecting system 1012. The reconstructing unit 1024 has a function of averaging such redundant data. This makes it possible to suppress an abrupt change in image quality due to changes in the sensitivity of the first data detecting system 1011 and second data detecting system 1012.

In a scan cycle after the scan cycle including this failure occurrence time t, the apparatus completely switches to tomographic image reconstruction processing using the data acquired by the second data detecting system 1012.

As described above, even if a failure such as abnormal discharge occurs in the process of a scan, or a detector cannot be used due to a channel failure, a helical scan can be continued by switching data acquisition from the first data detecting system 1011 to the second data detecting system 1012. Obviously, in this case, a failure indicates a situation in which data acquisition cannot be done. In this sense, a failure factor is not limited to abnormal discharge in an X-ray tube, and may include an emission failure due to other factors such as a failure in a cooling system, and a failure in an X-ray detector or data acquiring unit. It is apparent that the present invention can be applied to such failure factors.

A case of a single-slice scan will be described next. In this case, a half scan will be exemplified. Note that a case wherein a failure such as abnormal discharge has occurred in the first X-ray tube 1111 will be described as well. A case wherein the first X-ray detector 1113 cannot be used due to the occurrence of a channel failure is handled in the same manner as the case wherein a failure such as abnormal discharge has occurred in the first X-ray tube 1111.

Figure 6:
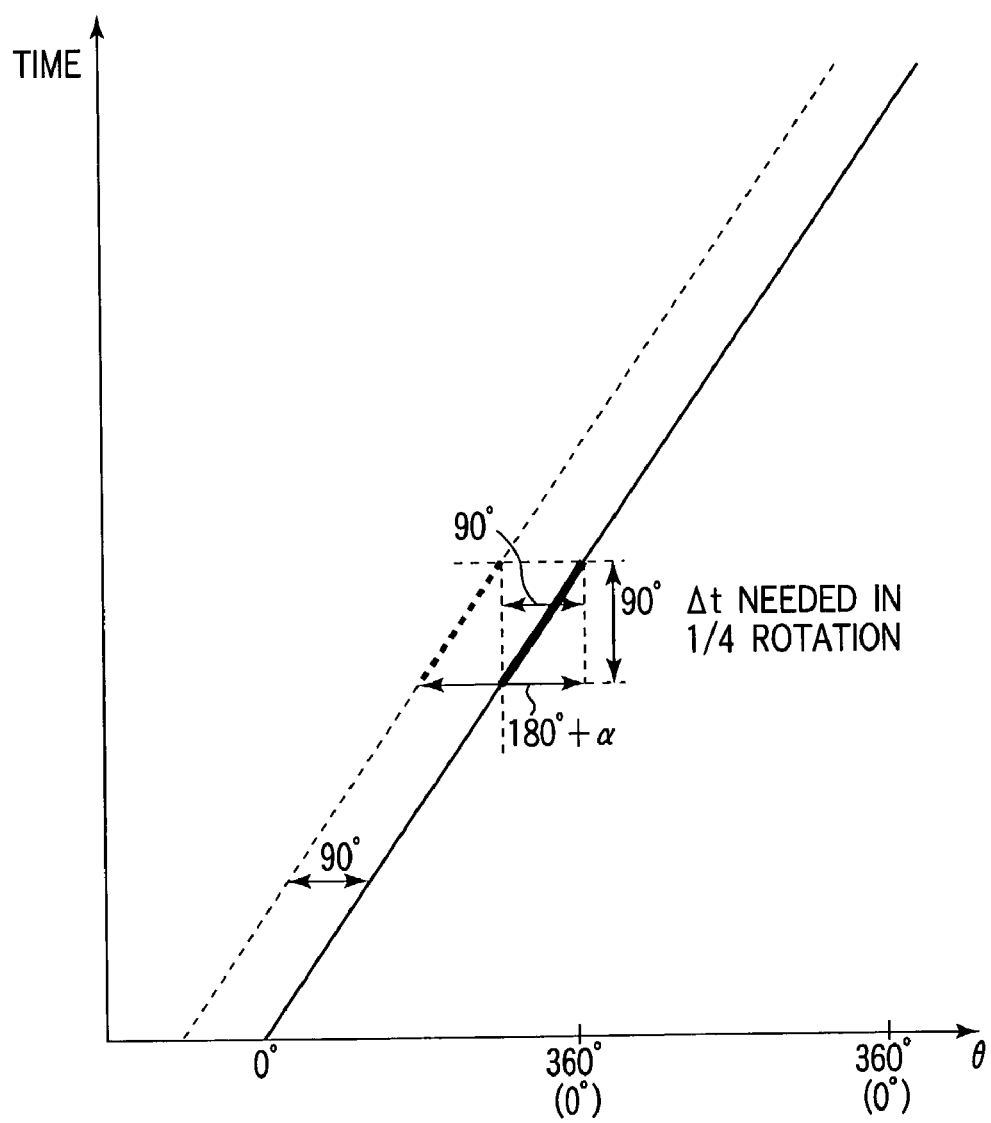
FIG. 6 is a graph for explaining the scan continuation function in a single-slice scan according to this embodiment.

A single-slice scan is the operation of repeatedly scanning a single slice by continuously rotating X-ray tubes while fixing a table-top. FIG. 6 shows the orbits of the first and second X-ray tubes 1111 and 1121 in a single-slice scan, with the ordinate and abscissa representing time and the rotation angle, respectively. When a single-slice scan mode is designated, the moving unit 1016 sets the Z-position of the second data detecting system 1012 at the same position as the Z-position of the first data detecting system 1011, i.e., at a position where the second data detecting system 1012 continuously acquires projection data of the same slice as that scanned by the first data detecting system 1011.

In this single-slice scan operation, in a period during which both the first and second X-ray tubes 1111 and 1121 are normal, projection data are acquired by both the first and second data detecting systems 1011 and 1012, and the data acquired by the two data detecting systems are mixed to prepare data corresponding to 180°+α which is required for the construction of one tomographic image, thereby reconstructing tomographic image data on the basis of the mixed data. As a consequence, as shown in FIG. 6, the scan cycle can be shortened to a time Δt required for 90° rotation. That is, the time resolution of a tomographic image can be doubled as compared with the case wherein one data detecting system is used.

Figure 7:
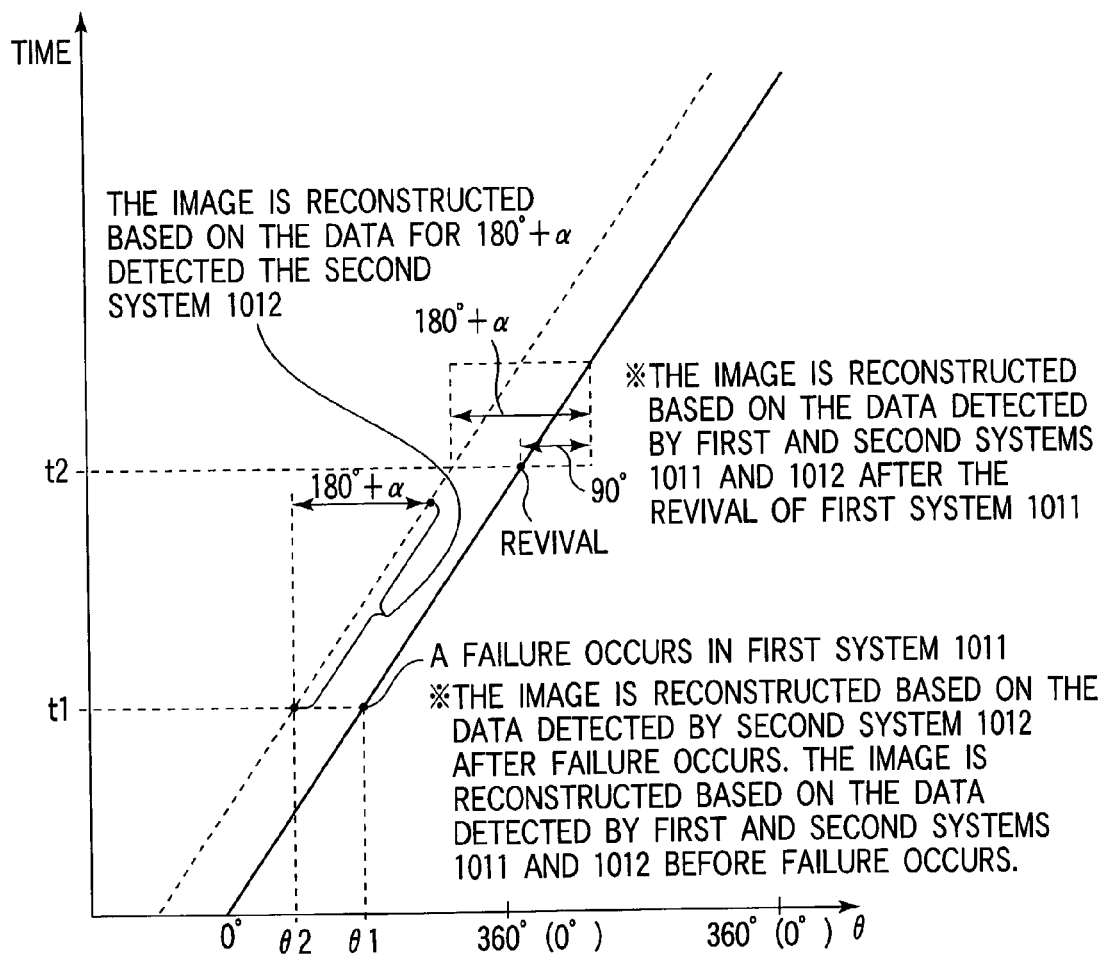
FIG. 7 is a graph for explaining in detail the scan continuation function in a single-slice scan according to this embodiment.

FIG. 7 is a graph for explaining operation to be done when a failure such as abnormal discharge occurs in the first X-ray tube 1111. Referring to FIG. 7, at time t1, a failure such as abnormal discharge has occurred in the first X-ray tube 1111.

At time t1, the first X-ray tube 1111 is located at the rotation angle θ1, and the second X-ray tube 1121 is located at the rotation angle θ2 which is 90° behind the rotation angle θ1. At time t1, the scan control unit 1014 stops applying a tube voltage to the first X-ray tube 1111 and stops supplying a filament heating current thereto. At the same time, the scan control unit 1014 stops the data acquisition done by the first data detecting system 1011. Meanwhile, the scan control unit 1014 continues to apply a tube voltage to the second X-ray tube 1121 and supply a filament heating current thereto. In addition, the scan control unit 1014 continues the data acquisition done by the second data detecting system 1012.

Furthermore, in accordance with the automatic revival function, the scan control unit 1014 resumes applying a tube voltage to the first X-ray tube 1111 and supplying a filament heating current thereto. When a failure factor is abnormal discharge, the possibility of success of automatic revival is high.

Tomographic image reconstruction processing may be performed concurrently with the single-slice scan to realize so-called CT fluoroscopy, or may be non-real-time processing that is started after the single-slice scan.

As described above, with regard to tomographic image reconstruction, in a scan cycle before failure occurrence time t1, the data acquired by both the first and second data detecting systems 1011 and 1012 are mixed to prepare data corresponding to 180°+α which is required for the construction of one tomographic image, and tomographic image data is reconstructed on the basis of the mixed data.

In the period from failure occurrence time t1 to revival time t2, tomographic image data is repeatedly reconstructed on the basis of only the projection data acquired by the second data detecting system 1012 which corresponds to an angle (360° or 180°+α (fan angle)) required for the reconstruction of one tomographic image. In this period, as in a one-tube system, the scan cycle in the second data detecting system 1012 is prolonged to a time Δt required for 180°+α rotation, and the time resolution of a tomographic image decreases to ½ within this period. However, the scan can be continued without being stopped.

After revival time t2, high-time-resolution operation is restored, in which the data acquired by both the first and second data detecting systems 1011 and 1012 are mixed to prepare data corresponding to 180°+α which is required to reconstruct one tomographic image, and tomographic image data is reconstructed on the basis of the mixed data.

As described above, even if a failure such as abnormal discharge occurs, the scan itself can be continued although the time resolution decreases. Obviously, in this case, a failure indicates a situation in which data acquisition cannot be done. In this sense, a failure factor is not limited to abnormal discharge in an X-ray tube, and may include an emission failure due to other factors such as a failure in a cooling system, and a failure in an X-ray detector or data acquiring unit. It is apparent that the present invention can be applied to such failure factors.

(Second Embodiment)

Figure 8:
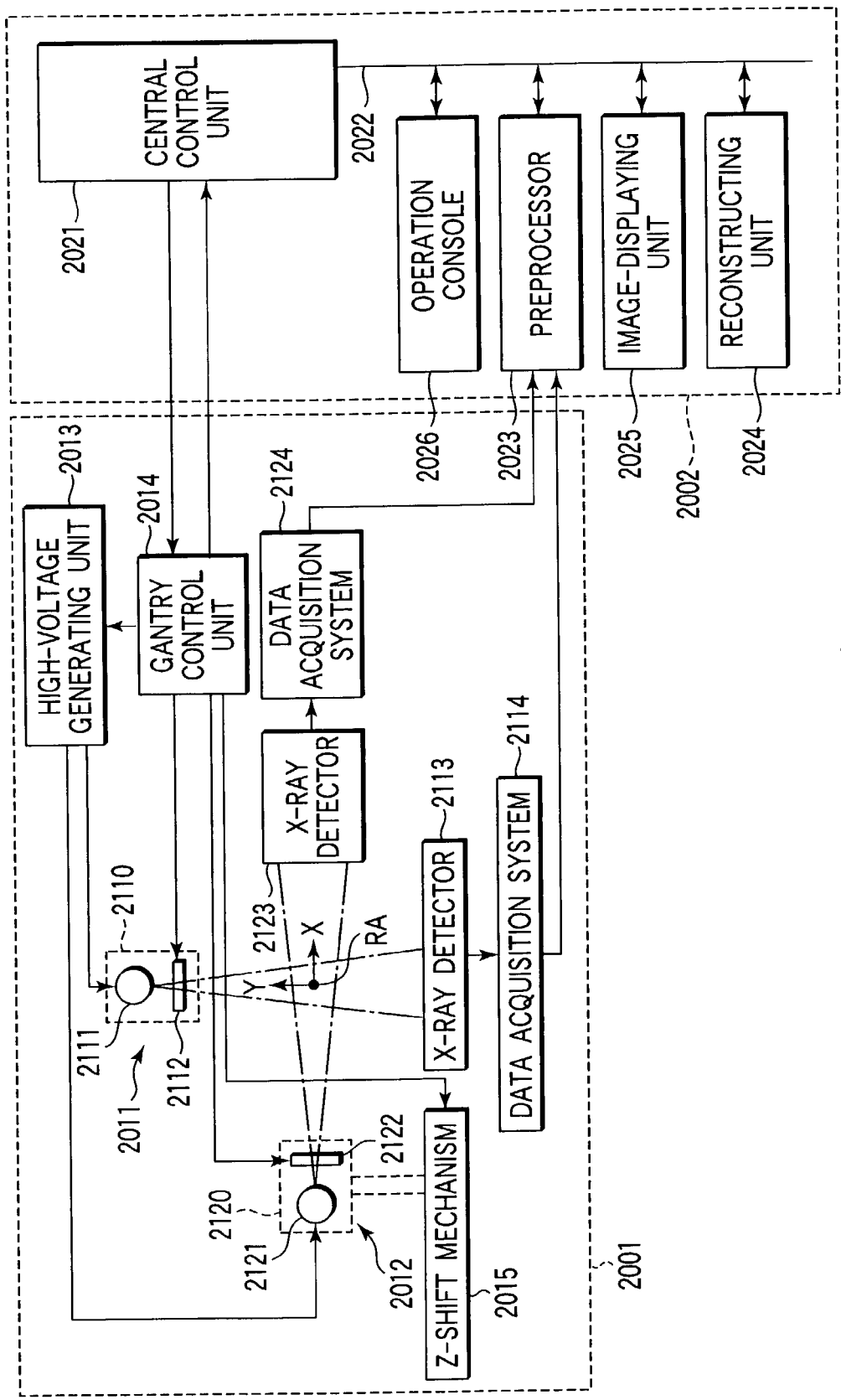
FIG. 8 is a block diagram showing the arrangement of the main part of an X-ray computed tomography apparatus according to the second embodiment of the present invention.

FIG. 8 shows the arrangement of the main part of an X-ray computed tomography apparatus according to the second embodiment. The X-ray computed tomography apparatus according to this embodiment is comprised of a scan gantry 2001 and a computer device 2002 (not shown). In the computer device 2002, a preprocessor 2023, a reconstructing unit 2024, an image displaying unit 2025, and an operation console 2026 are connected to a central control unit 2021 via a data/control bus 2022.

The scan gantry 2001 is of a multi-tube type, i.e., has a plurality of data detecting systems, each including an X-ray tube assembly and X-ray detector. In this case, the scan gantry 2001 will be described as a two-tube type gantry. A first data detecting system 2011 is comprised of a first X-ray tube assembly 2110 and first X-ray detector 2113. The first X-ray tube assembly 2110 is mounted together with the first X-ray detector 2113 on a rotating gantry which rotates about a rotation center axis RA. A second data detecting system 2012 constituted by a second X-ray tube assembly 2120 and second X-ray detector 2123 is also mounted on the same rotating gantry or a different rotating gantry via a Z-shift mechanism 2015.

The first X-ray tube assembly 2110 is comprised of a first X-ray tube 2111 and diaphragm device 2112. The second X-ray tube assembly 2120 is comprised of a second X-ray tube 2121 and diaphragm device 2122. In this case, a line connecting the X-ray focal point of the first X-ray tube 2111 and the center of the first X-ray detector 2113 is termed the first center. Likewise, a line connecting the X-ray focal point of the second X-ray tube 2121 and the center of the second X-ray detector 2123 is termed the second center line. The positions of the first and second data detecting systems 2011 and 2012 are designed such that the first and second center lines cross the rotation center axis RA, and the second center line is shifted from the first center line around the rotation center axis RA by a predetermined angle, e.g., 90°.

The Z-shift mechanism 2015 has a structure and power source which are required to move at least one of the first and second data detecting systems 2011 and 2012, the second data detecting system 2012 in this case, along the rotation center axis RA. The movement of the second data detecting system 2012 by the Z-shift mechanism 2015 allows the center line of the second data detecting system 2012 to be shifted forward/backward with respect to the center line of the first data detecting system 2011 by an arbitrary distance from the initial state wherein the center line of the second data detecting system 2012 crosses the center line of the first data detecting system 2011.

A high voltage generating unit 2013 is designed to separately apply tube voltages to the first and second X-ray tubes 2111 and 2121 and supply filament heating currents thereto.

Figure 9:
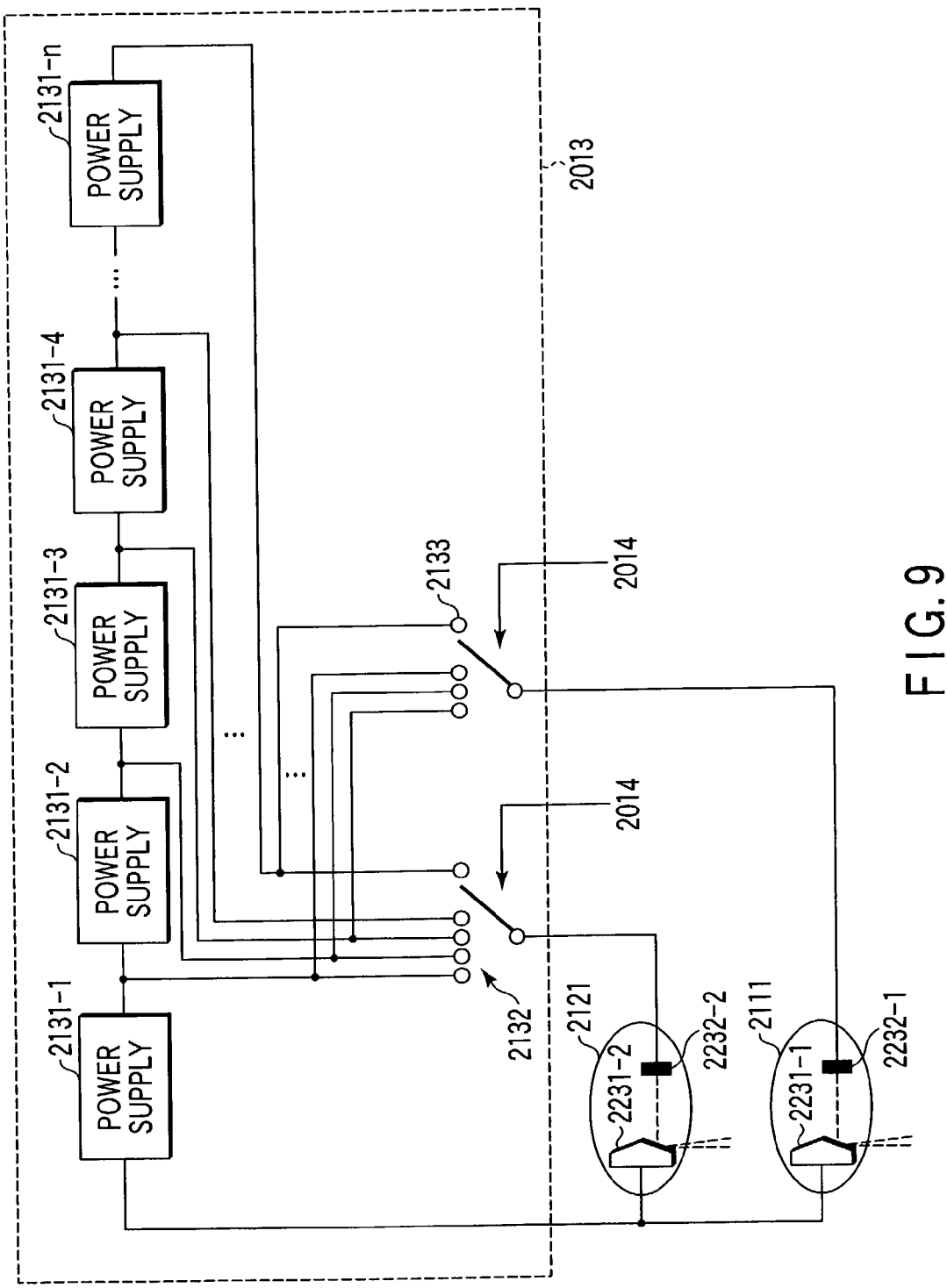
FIG. 9 is a view showing the arrangement of a high voltage generating unit in FIG. 8.

FIG. 9 shows an example of the arrangement of the tube voltage generating portion of the high voltage generating unit 2013. The high voltage generating unit 2013 is shared by the first X-ray tube 2111 and second X-ray tube 2121. However, high voltage generating devices may be provided for the first X-ray tube 2111 and second X-ray tube 2121, respectively. The high voltage generating unit 2013 generates tube voltages to be applied between the anodes and the cathodes. In addition, the high voltage generating unit 2013 generates filament heating currents for heating the filaments. The high voltage generating unit 2013 has a plurality of power supplies 2131-1, 2131-2, . . . , 2131-n. The plurality of power supplies 2131-1, 2131-2, . . . , 2131-n have the same fixed output capacity, e.g., 40 kV. However, the plurality of power supplies need not have the same output performance. For example, the first power supply 2131-1 whose positive terminal is connected to anodes 2231-1 and 2231-2 of the first and second X-ray tubes 2111 and 2121 may have a capacity of 60 kV, whereas the remaining power supplies 2131-2, . . . , 2131-n may have a capacity of 20 kV.

The negative terminals of the power supplies 2131-1, . . . , 2131-n are selectively connected to a cathode 2232-1 of the first X-ray tube 2111 via a selector 2133. The voltage applied between the anode and cathode of the first X-ray tube 2111 can be changed in steps of 20 kV in the range from 60 kV to (60+20×(n−1)) kV by selection done by the selector 2133.

Likewise, the negative terminals of the power supplies 2131-1, . . . , 2131-n are selectively connected to a cathode 2232-2 of the second X-ray tube 2121 via a selector 2132. The voltage applied between the anode and cathode of the second X-ray tube 2121 can be changed in steps of 20 kV in the range from 60 kV to (60+20×(n−1)) kV by selection done by the selector 2132.

Selection done by the selector 2133 is independent of selection done by the selector 2132. The high voltage generating unit 2013 can therefore apply different tube voltages to the first and second X-ray tubes 2111 and 2121. Obviously, the high voltage generating unit 2013 can apply the same tube voltage to the first and second X-ray tubes 2111 and 2121.

Outputs from the first and second X-ray detectors 2113 and 2123 are respectively supplied to the preprocessor 2023 of the computer device 2002 via data acquiring units 2114 and 2124 and a slip ring (not shown) that allows continuous rotation. The preprocessor 2023 takes charge of processing the data sent from the data acquiring units 2114 and 2124 (the data in this stage is generally called raw data) into data used for reconstruction processing (the data in this stage is generally called projection data). This processing typically includes so-called reference correction processing in which variations in X-ray irradiation dose due to variations in tube voltages and tube currents to the X-ray tubes 2111 and 2121 are detected by reference detectors, and raw data are normalized in accordance with the detected values, thereby correcting the variations in X-ray irradiation dose, and water correction processing in which X-ray absorption by wedge filters and the like and the sensitivity difference between the channels of detectors are canceled out by subtracting the raw data of a water phantom which has been acquired in advance from the raw data of a subject P to be examined. This processing may also include beam hardening correction processing, body movement correction processing, and the like.

The reconstructing unit 2024 reconstructs tomographic image data on the basis of the projection data preprocessed by the preprocessor 2023. This tomographic image data is displayed on the image displaying unit 2025.

Figures 10A, 10B:
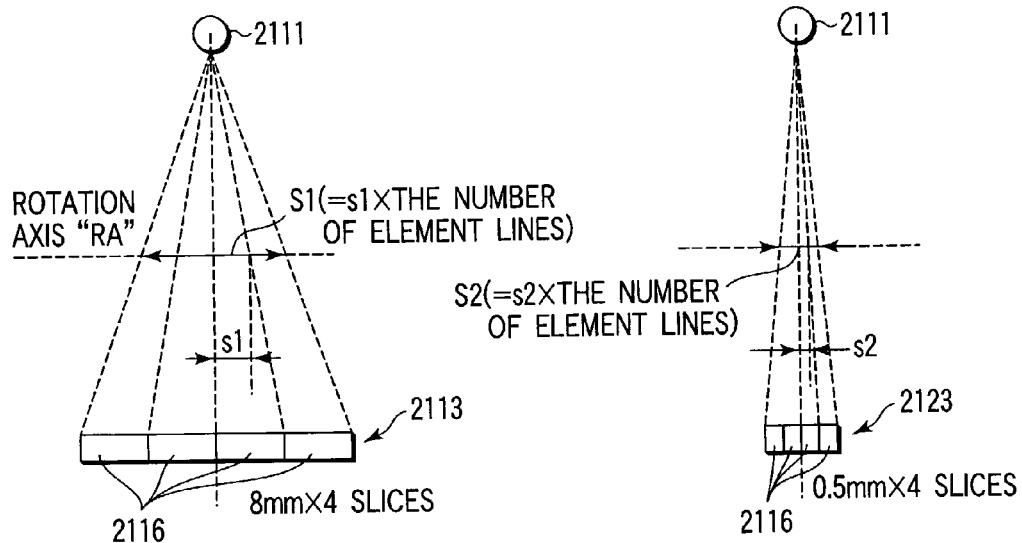
FIGS. 10A and 10B are views showing the slice thicknesses of the first and second data detecting systems in FIG. 8.
Figure 11A:
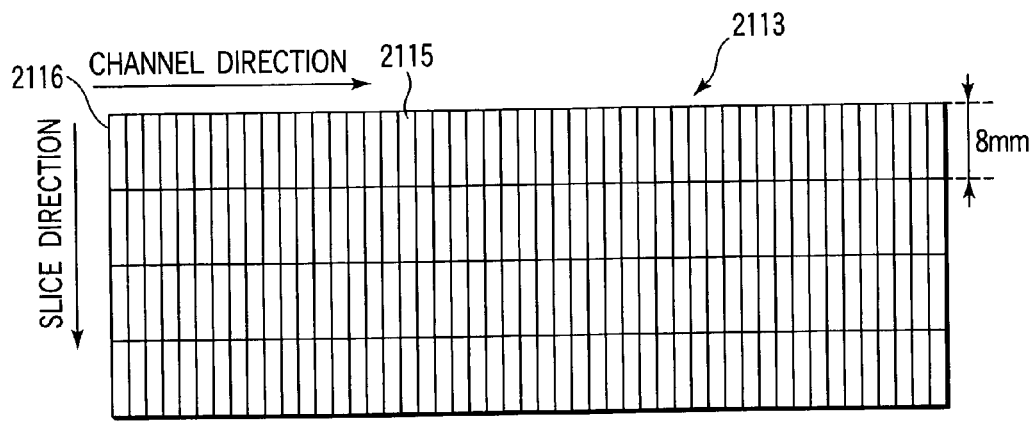
FIGS. 11A and 11B are plan views of the first and second X-ray detectors in FIG. 8.

FIG. 10A is a side view of the first X-ray detector 2113. FIG. 11A is a plan view of the first X-ray detector 2113. The first X-ray detector 2113 has a plurality of (four in this case) first detection element lines 2116. The four first detection element lines 2116 are juxtaposed such that their longitudinal direction becomes parallel to the slice direction (rotation center axis RA). Each first detection element line 2116 is constituted by a plurality of first detection elements 2115 arrayed in a line in the slice direction. Each first detection element 2115 has a sensitive area having the first width in the slice direction. The first width is set to correspond to a slice thickness s1, e.g., 8 mm. Therefore, the first data detecting system 2011 can simultaneously acquire four consecutive 8-mm thick slice data. Note that the product of the slice thickness s1 and the number of element lines will be referred to as a total slice thickness S1 of the first data detecting system 2011.

Figure 11B:
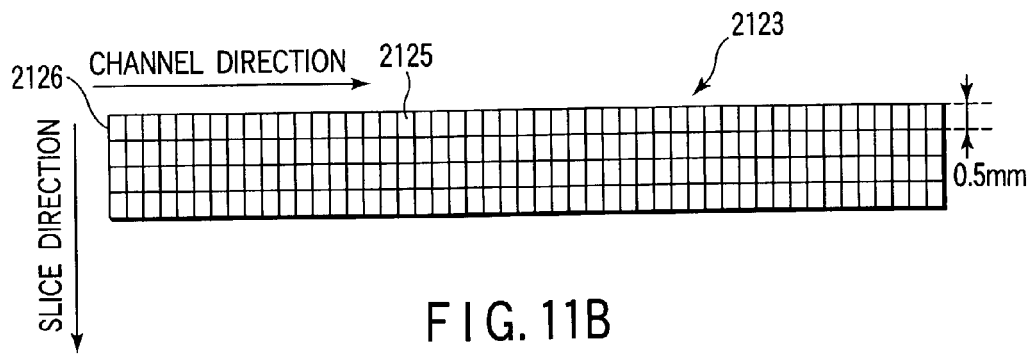

FIG. 10B is a side view of the second X-ray detector 2123. FIG. 11B is a plan view of the second X-ray detector 2123. The second X-ray detector 2123 has a plurality of (four in this case like the first X-ray detector 2113) second detection element lines 2126. The four second detection element lines 2126 are juxtaposed such that their longitudinal direction becomes parallel to the slice direction (rotation center axis RA). Each second detection element line 2126 is constituted by a plurality of second detection elements 2125 arrayed in a line in the slice direction. Each second detection elements 2125 has a sensitive area having the same width as that of the first detection element 2115 in the channel direction and a second width smaller than the first width in the slice direction. The second width is designed to be, for example, a slice thickness s2 of 0.5 mm. Therefore, the second data detecting system 2012 can simultaneously acquire four consecutive 0.5-mm thick slice data. Note that the product of the slice thickness s2 and the number of element lines will be referred to as a total slice thickness S2 of the second data detecting system 2012.

Figure 12:
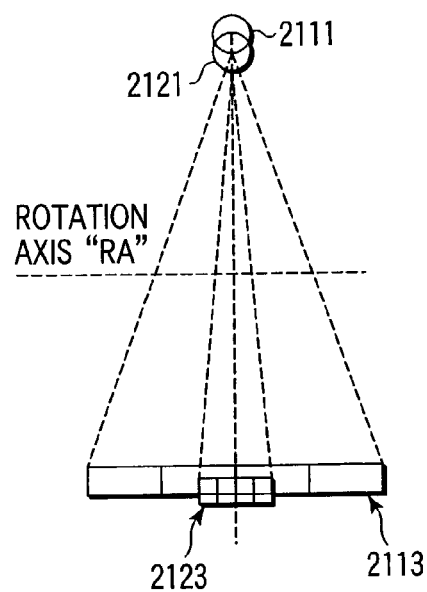
FIG. 12 is a view showing the positions of the first and second data detecting systems in FIG. 8 in the first position mode.

With respect to the first and second data detecting systems 2011 and 2012, the central control unit 2021 has three types of control modes for the Z-shift mechanism 2015. These three types of control modes are selected by an operator through the operation console 2026. As shown in FIG. 12, in the first mode, control is performed to maintain or restore the initial state wherein the center line of the second data detecting system 2012 crosses the center line of the first data detecting system 2011. In the first mode, therefore, slice data having different slice thicknesses can be simultaneously acquired at the same position by the first and second data detecting systems 2011 and 2012.

From a clinical viewpoint, one scan allows the operator to roughly acquire overall internal information by acquiring data with a large slice thickness in a wide region and acquire detailed internal information of a portion near the center of the region by acquiring data with a small slice thickness.

Figure 13:
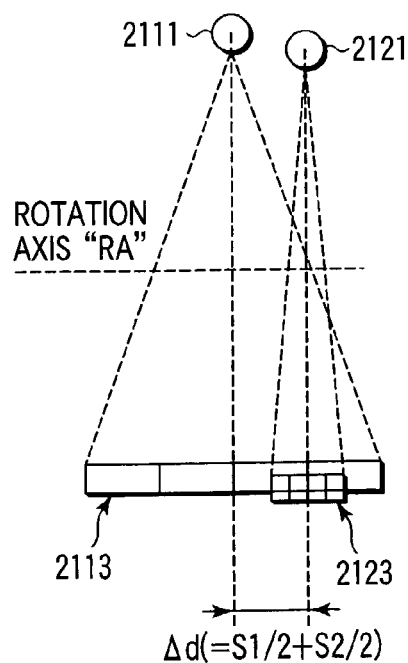
FIG. 13 is a view showing the positions of the first and second data detecting systems in FIG. 8 in the second position mode.
Figures 14A, 14B:
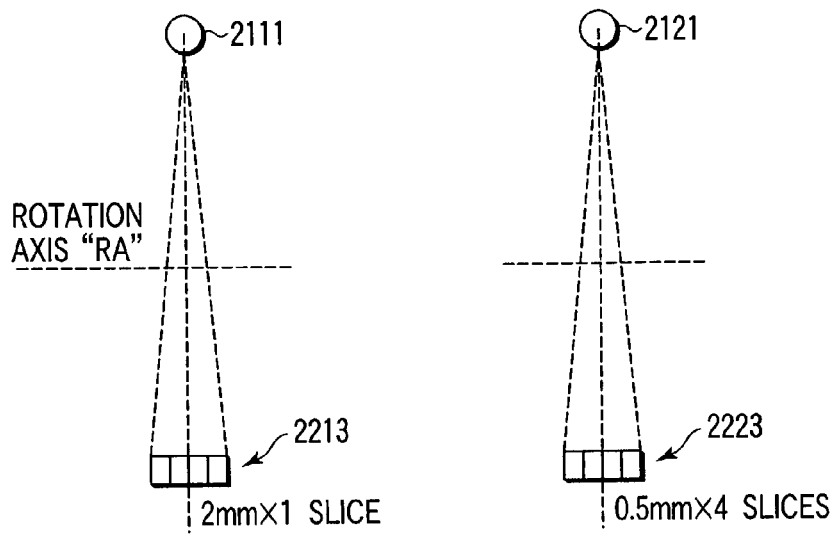
FIGS. 14A and 14B are views showing the slice thicknesses of the first and second data detecting systems in a modification of this embodiment.
Figure 15A:
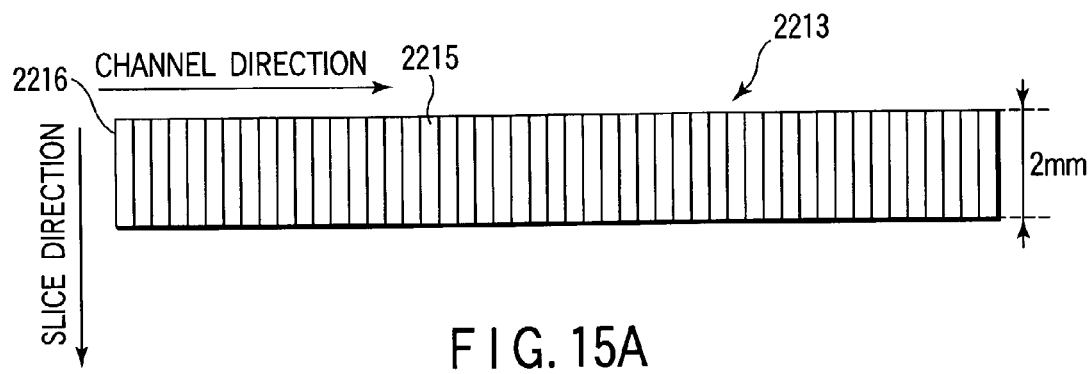
FIGS. 15A and 15B are plan views of the first and second X-ray detectors in FIGS. 14A and 14B.
Figure 15B:
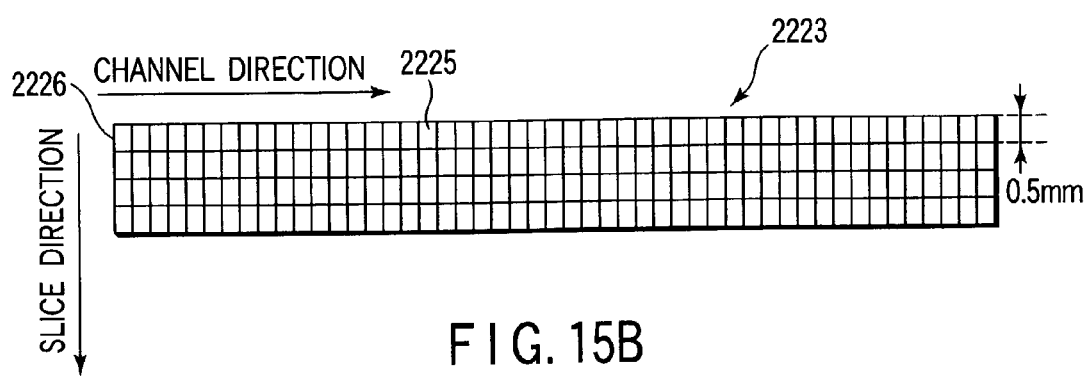

In the second mode, as shown in FIG. 13, control is performed to shift the center line of the second data detecting system 2012 from the center line of the first data detecting system 2011 by a predetermined distance Δd. The distance between the center line of the first data detecting system 2011 and the center line of the second data detecting system 2012 is determined by the sum of a distance corresponding to ½ the total slice thickness S1 of the first data detecting system 2011 and a distance corresponding to ½ the total slice thickness S2 of the second data detecting system 2012. As described above, in the second mode, a plurality of (eight in this case) consecutive slice data which change in slice thickness halfway can be simultaneously acquired by setting the first and second data detecting systems 2011 and 2012 at a predetermined distance (S1/2+S2/2).

From a clinical viewpoint, one scan allows the operator to roughly acquire overall internal information by acquiring data with a large slice thickness in a wide region and acquire detailed internal information by acquiring data in a relatively narrow region adjacent to the wide region with a small slice thickness.

In the third mode, control is performed in accordance with instructions from the second data detecting system 2012 to arbitrarily set a distance between the center line of the first data detecting system 2011 and the center line of the second data detecting system 2012. In the third mode, the data of slices having different slice thicknesses can be simultaneously acquired at different arbitrary positions by using the first and second data detecting systems 2011 and 2012. From a clinical viewpoint, one scan allows the operator to roughly acquire overall internal information by acquiring data with a large slice thickness in a wide region and acquire detailed internal information by acquiring data in a region of interest in which an affected part exists with a small slice thickness.

In a scan, the first and second data detecting systems 2011 and 2012 rotate at the same angular velocity, and the sensitive area of each detection element 2125 of the second data detecting system 2012 is smaller than that of each detection element 2125 of the first data detecting system 2011, i.e., the second data detecting system 2012 is lower in sensitivity than the first data detecting system 2011. In order to correct this sensitivity difference, the central control unit 2021 sets the dose of X-rays emitted from the second X-ray tube 2121 to be higher than the dose of X-rays emitted from the first X-ray tube 2111 in executing a scan. More specifically, a tube voltage TV1 applied to the first X-ray tube 2111 is set to be equal or almost equal to a tube voltage applied to the second X-ray tube 2121, while the filament heating current (tube current: TC1) supplied to the first X-ray tube 2111 is set to be smaller than the filament heating current (tube current: TC2) supplied to the second X-ray tube 2121. For example, the tube current supplied to the second X-ray tube 2121 is set to 250 mA, and the tube current supplied to the first X-ray tube 2111 is set to 50 mA.

The slice thickness of the first data detecting system 2011 is small, and the slice thickness of the first data detecting system 2011 is large. In the first data detecting system 2011, hard radiation is effective in improving the high contrast performance and the visibility of a fine region. In contrast, in the second data detecting system 2012, soft radiation is effective in improving the low contrast performance and increasing the density. For this purpose, a relatively low tube voltage of, e.g., 80 kV is applied from the high voltage generating unit 2013 to the X-ray tube 2111 of the first data detecting system 2011, whereas a relatively high tube voltage of, e.g., 140 kV is applied from the high voltage generating unit 2013 to the second X-ray tube 2121.

As described above, according to this embodiment, data about slices having different slice thicknesses and located at the same position can be simultaneously acquired by one scan, data about a plurality of slices having different slice thicknesses can be simultaneously acquired as consecutive slices by one scan, and data about a plurality of slices having different slice thicknesses can be simultaneously acquired by one scan.

As shown in FIGS. 14A, 14B, 15A, and 15B, a first X-ray detector 2213 may be constituted by one detection element line 2213 corresponding to a slice thickness of, e.g., 2 mm, and a second X-ray detector 2223 may be constituted by four detection element lines 2223 corresponding to a slice thickness of, e.g., 0.5 mm such that the total slice thickness becomes equal to the slice thickness of the detection element line 2213. In this case, data about a 2-mm thick slice and data about four slices whose total slice thickness is 0.5 mm×4 can be simultaneously acquired. From a clinical viewpoint, data in the same region can be roughly observed with one thick slice, and the interior can be observed in detail with a plurality of thin slices.

As shown in FIGS. 16A and 16B, a first X-ray detector 2313 may be constituted by four detection element lines 2316 corresponding to a slice thickness of, e.g., 2 mm, and a second X-ray detector 2323 is constituted by four detection element lines 2326 corresponding to a slice thickness of, e.g., 1 mm such that the total slice thickness becomes equal to the total slice thickness of two detection element lines 2316. In this case, as shown in FIG. 17, data acquisition is performed in a middle region with four thin slices, and at the same time, data can be acquired with thick slices having a slice thickness of 2 mm which are adjacent to the two sides of the four slices located in the middle region. From a clinical viewpoint, the middle region can be observed in detail with four thin slices, and two sides of the middle regions can be roughly observed with thick slices.

(Third Embodiment)

FIG. 18 shows the arrangement of the main part of an X-ray computed tomography apparatus according to this embodiment. The X-ray computed tomography apparatus according to this embodiment is comprised of a scan gantry 3001, a computer device 3002, and a bed (not shown). The scan gantry 3001 is a constituent element for acquiring projection data about a subject to be examined. This projection data is loaded into the computer device 3002 and subjected to processing such as image reconstruction. The subject is inserted into the imaging area of the scan gantry 3001 while lying on the table-top of the bed.

The computer device 3002 is comprised of a central control unit 3021 and the following units connected thereto via a data/control bus 3022: a data complementing unit 3023, image reconstructing unit 3024, and image display unit 3025.

The scan gantry 3001 of a multi-tube type, i.e., has a plurality of data detecting systems, each including an X-ray tube assembly and X-ray detector, mounted on an annular rotating gantry. In this case, the scan gantry 3001 will be described as a two-tube type gantry. In a first data detecting system 3011, a first X-ray tube assembly 3110 and a first X-ray detector 3113 which faces it are mounted on the rotating gantry. In a second data detecting system 3012, a second X-ray tube assembly 3120 and a second X-ray detector 3123 which faces it are mounted on the rotating gantry such that the central axis of the second data detecting system 3012 crosses the central axis of the first data detecting system 3011 at a rotation axis RA at a predetermined angle (assumed to be 90° herein), and the second data detecting system 3012 is located at a position where it scans the same slice as that scanned by the first data detecting system 3011.

The first X-ray tube assembly 3110 is comprised of a first X-ray tube 3111 and peripheral elements arranged between the first X-ray tube 3111 and the subject, e.g., a first X-ray collimator 3112 mounted at a position immediately in front of the X-ray radiation window of the first X-ray tube 311. The first X-ray collimator 3112 limits the divergence angle (fan angle or viewing angle) of X-rays emitted from the first X-ray tube 3111. The first X-ray collimator 3112 has a plurality of movable shield plates and driving units which separately move the plates. The aperture width and aperture center position can be arbitrarily adjusted by controlling the position of each of the plurality of movable shield plates.

The second X-ray tube assembly 3120 is also comprised of a second X-ray tube 3121 and peripheral elements such as a second X-ray collimator 3122. The second X-ray collimator 3122 also limits the divergence angle (fan angle) of X-rays emitted from the second X-ray tube 3121. The second X-ray collimator 3122 has a plurality of movable shield plates and driving units which separately move the plates. The aperture width and aperture center position can be arbitrarily adjusted by controlling the position of each of the plurality of movable shield plates.

A high voltage generating unit 3013 has high voltage generators of two systems corresponding to the first and second X-ray tubes 3111 and 3121 so as to separately apply and supply tube voltages and filament heating currents (tube currents are controlled by the filament heating currents) to the first and second X-ray tubes 3111 and 3121. Tube voltages and filament heating currents are applied/supplied from these high voltage generators of the two systems to the first and second X-ray tubes 3111 and 3121 under the control of a scan control unit 3014. In addition to the control on the high voltage generating unit 3013, the scan control unit 3014 takes charge of all operation control required for a scan, e.g., setting of the aperture widths and aperture center positions of the first and second X-ray collimators 3112 and 3122, the rotation of the rotating gantry, and the movement of the table-top.

Outputs from the first and second X-ray detectors 3113 and 3123 are supplied as projection data to the computer device 3002 via data acquiring units 3114 and 3124, a slip ring (not shown) which allows continuous rotation, and the preprocessor. The data complementing unit 3023 of the computer device 3002 complements missing part of the projection data obtained by the second X-ray detector 3123 with the projection data obtained by the first X-ray detector 3113. The image reconstructing unit 3024 reconstructs tomographic image data on the basis of the complemented projection data. This data is then displayed on the image display unit 3025.

FIG. 19 shows the aperture widths of the first and second X-ray collimators 3112 and 3122 which are adjusted by the scan control unit 3014. The aperture width of the second X-ray collimator 3122 is set to be larger than that of the first X-ray collimator 3112. An aperture width A1 of the first X-ray collimator 3112 is set in accordance with a field of view FOV to irradiate the entire area of a subject slice with X-rays from the first X-ray tube 3111. An aperture width A2 of the second X-ray collimator 3122 is set to be relatively small in accordance with the ROI to exclusively irradiate only a region of interest ROI in a subject slice with X-rays from the second X-ray tube 3121 without irradiating portions other than the region of interest. In practice, the respective aperture widths may be set to standard values corresponding to parameters such as the physique of the subject and the type of region of interest or may be set to values unique to the subject from a tomographic image obtained by a prescan at a low dose.

As described above, a scan is performed with different aperture widths. In a scan, the dose of X-rays emitted from the first X-ray tube 3111 is lower than that from the second X-ray tube 3121. More specifically, a tube voltage TV1 applied to the first X-ray tube 3111 is set to be equal or almost equal to a tube voltage TV1 applied to the second X-ray tube 3121, whereas the filament heating current (tube current: TC1) supplied to the first X-ray tube 3111 is set to be smaller than the filament heating current (tube current: TC2) supplied to the second X-ray tube 3121. For example, the tube current supplied to the second X-ray tube 3121 is set to 250 mA, and the tube current supplied to the first X-ray tube 3111 is set to 50 mA. By setting the same tube voltages and different tube currents in this manner, soft or hard radiation can be set exclusively although different irradiation doses are set.

The projection data detected by the first and second X-ray detectors 3113 and 3123 in a scan with these settings are supplied to the data complementing unit 3023 of the computer device 3002. In the second data detecting system 3012, X-rays do not cover the entire area of a subject slice, and hence a tomographic image cannot practically be reconstructed from only the projection data detected by the second X-ray detector 3123. That is, data are omitted in some of the channels of the second X-ray detector 3123 due to the small aperture width. The data complementing unit 3023 complements such omitted channel data with the projection data on corresponding channels of the first X-ray detector 3113.

Figure 20:
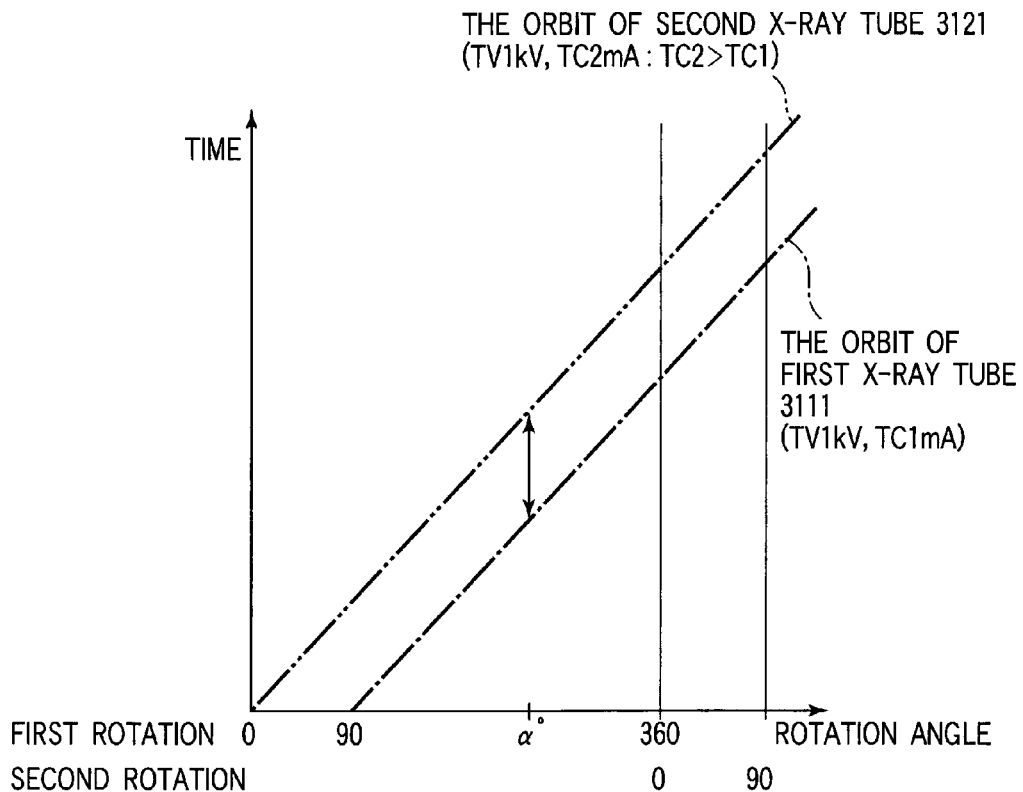
FIG. 20 is a graph showing the orbits of the first and second X-ray tubes in FIG. 18.
Figure 21:
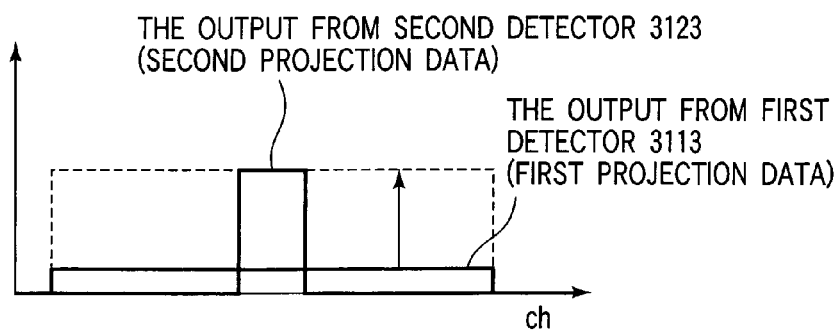
FIG. 21 is a view schematically showing the projection data respectively obtained by the first and second data detecting systems in FIG. 18.

FIG. 20 shows the orbits of the first and second X-ray tubes 3111 and 3121. The second X-ray tube 3121 is located at a position corresponding to a delay of 90° with respect to the first X-ray tube 3111, and hence draws an orbit delayed from that drawn by the first X-ray tube 3111 by 90°. Consider a rotation angle $\alpha°$. FIG. 21 shows the projection data distribution detected by the second X-ray detector 3123 when the second X-ray tube 3121 is located at the rotation angle $\alpha°$. Obviously, data on channels corresponding to a portion which is not irradiated with X-rays are omitted. The projection data on channels in which data omission has occurred are completed with the projection data on the same channels which are detected by the first X-ray detector 3113 when the first X-ray tube 3111 is located at the same rotation angle $\alpha°$.

In practice, since different X-ray irradiation doses are set, and different reference levels are set accordingly, projection data are weighted/added to make reference levels uniform. Letting $\theta$ be the rotation angle, ch be the channel, PD1 be the projection data detected by the first X-ray detector 3113, and PD2 be the projection data detected by the second X-ray detector 3123, the projection data PD output from the data complementing unit 3023 is given by $$PD(\theta, ch)=a \cdot PD1(\theta, ch)+b \cdot PD2(\theta, ch)$$

where $a$ and $b$ are weighting factors, their relationship is expressed as a>b, and these values are set to satisfy a=c·b where $c$ is the irradiation dose ratio of the first X-ray tube 3111 to the second X-ray tube 3121. Assuming that the irradiation dose $c$ is (50 mA/250 mA)=⅕, a=5 and b=1 are set.

In practice, the following processing is typical. The weighting factors are changed to a=5 and b=0 on a channel in the second data detecting system 3012 on which data omission has occurred, and the weighting factors are changed to a=0 and b=1 on a channel in the second data detecting system 3012 on which no data omission has occurred, thereby complementing only the data of the channel on which data omission has occurred with the projection data acquired by the first data detecting system 3011.

By using both X-rays with a narrow fan angle and a high irradiation dose and X-rays with a wide fan angle and a low irradiation dose, high resolution and high image quality can be realized with respect to a necessary portion, i.e., a region of interest, while the exposure dose can be suppressed low as compared with the case wherein a region of interest and the entire remaining regions are irradiated with X-rays at a high irradiation dose.

Figure 22:
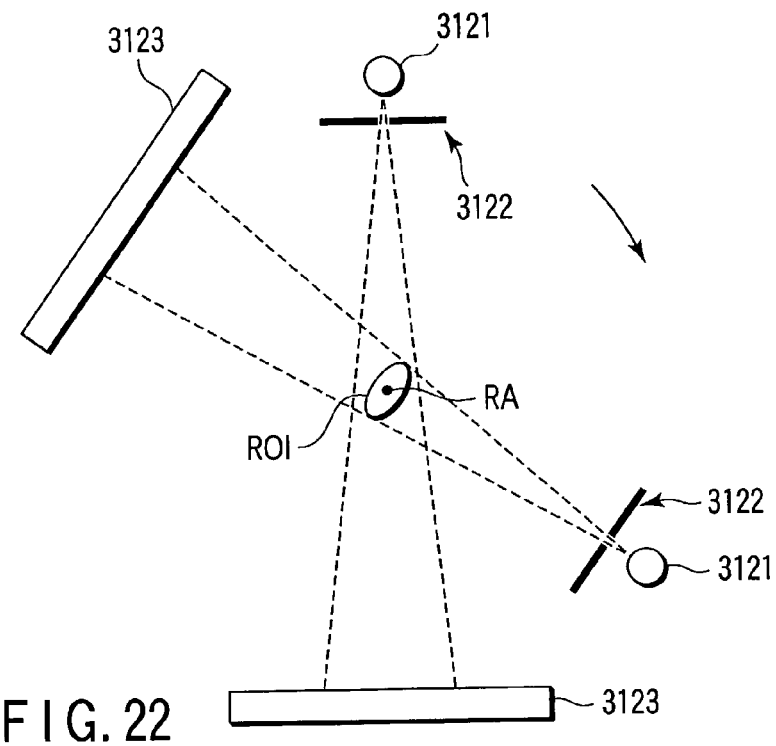
FIG. 22 is a view showing a state wherein when a region of interest exists on a rotation axis, the aperture width and aperture position of the second X-ray collimator under rotation do not change in this embodiment.

In an actual imaging procedure, the following procedure is required. A prescan is performed by using one of the data detecting systems 3011 and 3012 under the condition that the entire area of a subject slice is irradiated with X-rays at a low irradiation dose. A region of interest is then identified from the resultant tomographic image with a relatively low resolution. The aperture width of the second X-ray collimator 3122 is set in accordance with the size of the region of interest. In addition, as shown in FIG. 22, the state wherein the region of interest is located on the rotation axis RA is ensured by adjusting the table-top in the horizontal and vertical directions. In this state, the aperture position of the second X-ray collimator 3122 may be fixed during rotation.

Figure 23:
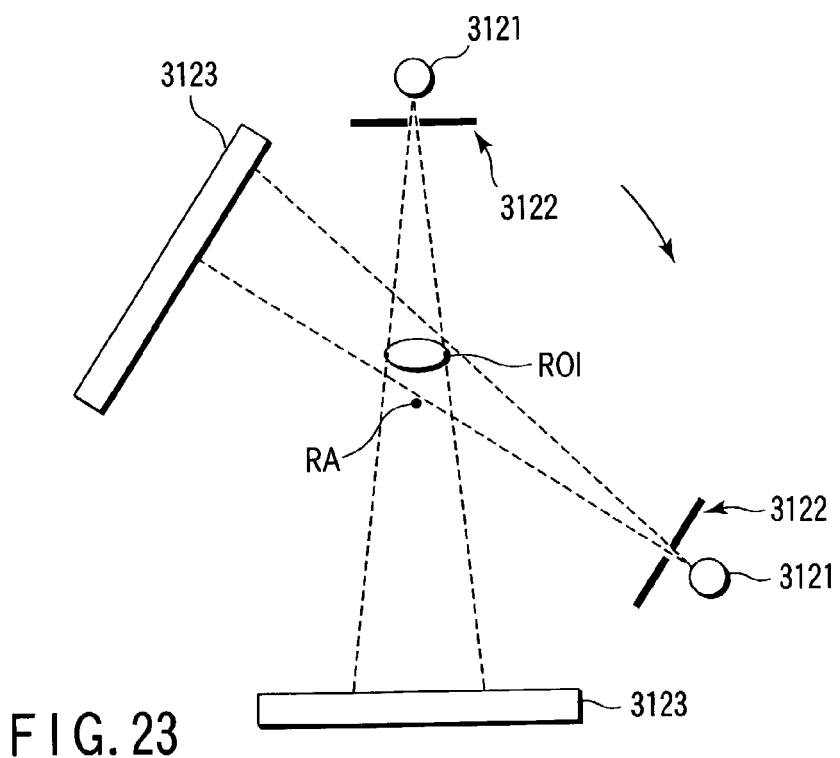
FIG. 23 is a view showing a state wherein when a region of interest exists at a position shifted from the rotation axis, the aperture width and aperture position of the second X-ray collimator under rotation change upon rotation in this embodiment.

As shown in FIG. 23, it may be impossible or difficult to ensure the state wherein a region of interest is located on the rotation axis RA. In this case, a wide aperture must be set to always capture a region of interest within the field of view of X-rays regardless of the rotation angle of the second X-ray tube 3121 in one rotation. With this setting, however, the exposure dose cannot be minimized. For this reason, the following operation is effective. The aperture of the second X-ray collimator 3122 is decreased in accordance with the size of the region of interest ROI. Subsequently, in order to always capture the region of interest within the narrow field of view of X-rays regardless of the rotation angle of the second X-ray tube 3121 in one rotation, the aperture position of the second X-ray collimator 3122 is moved in synchronism with the rotation angle.

The relationship between the aperture position of the second X-ray collimator 3122 and the rotation angle can be geometrically obtained from the positional relationship between the position of a region of interest on the tomographic image acquired in a prescan, the position of the rotation axis RA, and the position of the focal point of the second X-ray tube 3121. In accordance with the relationship between the aperture position of the second X-ray collimator 3122 and the rotation angle, the scan control unit 3014 can control the second X-ray collimator 3122 to move the aperture position of the second X-ray collimator 3122 in synchronism with the rotation angle.

(Fourth Embodiment)

Figure 24:
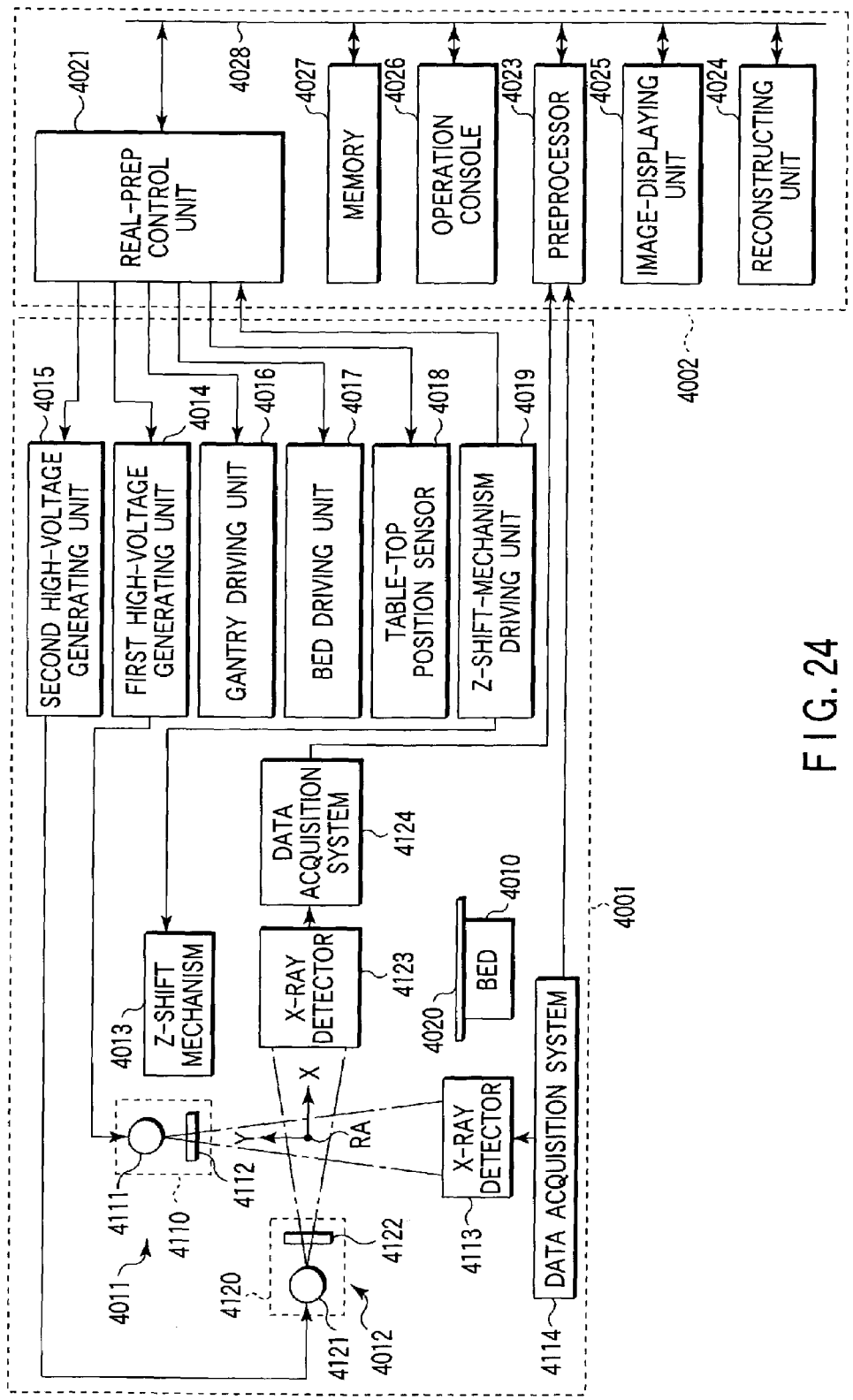
FIG. 24 is a block diagram showing the arrangement of the main part of an X-ray computed tomography apparatus according to the fourth embodiment of the present invention.

FIG. 24 shows the arrangement of the main part of an X-ray computed tomography apparatus according to the fourth embodiment. The X-ray computed tomography apparatus according to this embodiment is comprised of a scan gantry 4001 and computer device 4002. The scan gantry 4001 is a constituent element for acquiring projection data about a subject to be examined. This projection data is loaded into the computer device 4002 and subjected to processing such as image reconstruction. The computer device 4002 is comprised of a real-prep control unit 4021 and the following units connected thereto via a data/control bus 4028: a preprocessor 4023, image reconstructing unit 4024, image displaying unit 4025, operation console 4026, and memory 4027.

The subject is inserted into the scan gantry 4001 while lying on a table-top 4020 of a bed 4010. The table-top 4020 of the bed 4010 is driven by a bed driving unit 4017 to move along the longitudinal direction. In general, the bed 4010 is installed such that this longitudinal direction becomes parallel to a rotation axis RA (identical to the body axis and Z-axis). A table-top position sensor 4018 is provided to detect the position of the table-top 4020 and is formed from, for example, a rotary encoder.

An annular rotating gantry (not shown) is provided for the scan gantry 4001 so as to be driven by a gantry driving unit 4016 to rotate about the rotation axis RA. A plurality of data detecting systems, each constituted by an X-ray tube assembly, are mounted on this rotating gantry. In this case, two data detecting systems will be exemplified. In a first data detecting system 4011, which is one of the two systems, a first X-ray tube assembly 4110 and a first X-ray detector 4113 of a multi-channel type which opposes the first X-ray tube assembly 4110 are mounted on the rotating gantry. In a second data detecting system 4012, a second X-ray tube assembly 4120 and a second X-ray detector 4123 of a multi-channel type which opposes the second data detecting system 4012 are mounted on the rotating gantry such that the central axis of the second data detecting system 4012 crosses the central axis of the first data detecting system 4011 at the rotation axis RA at a predetermined angle (assumed to be 90° herein)

The first X-ray tube assembly 4110 is comprised of a first X-ray tube 4111 and a first X-ray filter 4112 for removing low-energy components to reduce the exposure dose. Likewise, the second X-ray tube assembly 4120 is comprised of a second X-ray tube 4121 and second X-ray filter 4122. A Z-shift mechanism 4013 is placed between the first X-ray tube assembly 4110 and the first X-ray detector 4113, and the rotating gantry. The Z-shift mechanism 4013 has a structure and power source which are required to support the first X-ray tube assembly 4110 and first X-ray detector 4113 so as to allow them to move in a direction parallel or almost parallel to the rotation axis RA. The Z-shift mechanism 4013 receives the power supplied from a Z-shift mechanism driving unit 4019 and electrically moves the first X-ray tube assembly 4110 and first X-ray detector 4113.

Inverter type high voltage generating units 4014 and 4015 of two systems are provided for the first and second X-ray tubes 4121 to separately supply power thereto. Each of the high voltage generating units 4014 and 4015 includes a tube voltage switch and filament current switch to adjust a tube voltage and filament current arbitrarily or stepwise.

Outputs from the first and second X-ray detectors 4113 and 4123 are supplied as projection data to an image reconstructing unit 4024 via data acquiring units 4114 and 4124, a slip ring (not shown) which allows continuous rotation, and a preprocessor 4023 and subjected to reconstruction processing of tomographic image data. This tomographic image data is displayed on an image displaying unit 4025 and also supplied to a real-prep control unit 4021 to be used for, for example, the processing of determining the start point of main-scan operation as will be described later.

An operation console 4026 is provided to allow the operator to input various information such as scan conditions (to be described later), a main-scan trigger, pre-trigger, and the like (to be described later). A memory 4027 is provided to store the data of input scan conditions and supply the data to the real-prep control unit 4021 at the proper timing along with the progress of an imaging sequence.

Control operation concerning contrast-medium imaging by the real-prep control unit 4021 will be described below. With regard to this control operation, the real-prep control unit 4021 is equipped with four types of operation modes which can be selectively used in accordance with an instruction of the operator. These four types of operation modes will be sequentially described below.

(First Control Operation)

Figure 25:
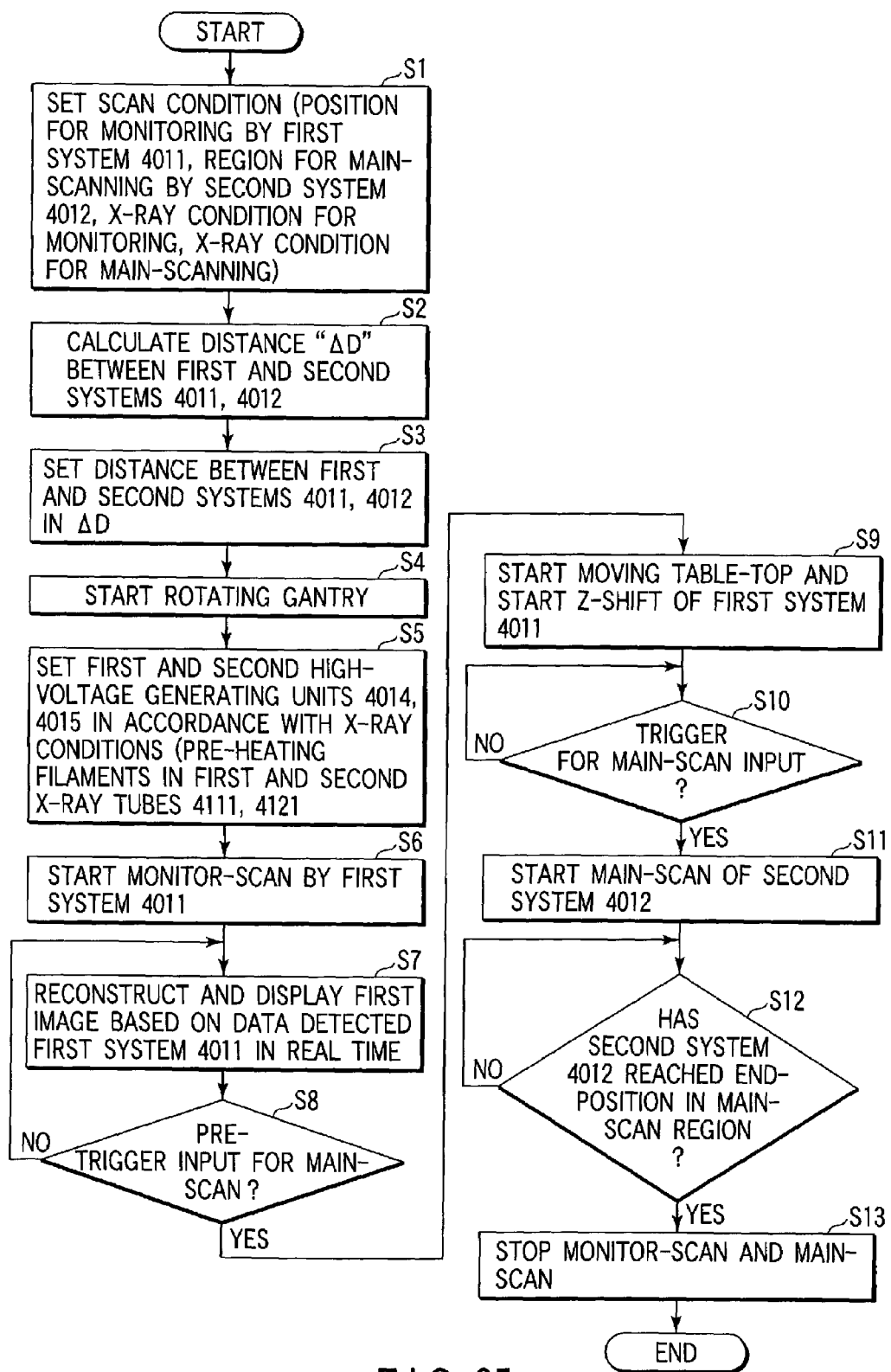
FIG. 25 is a flow chart showing the first control operation by a real-prep control unit in FIG. 24.
Figure 26:
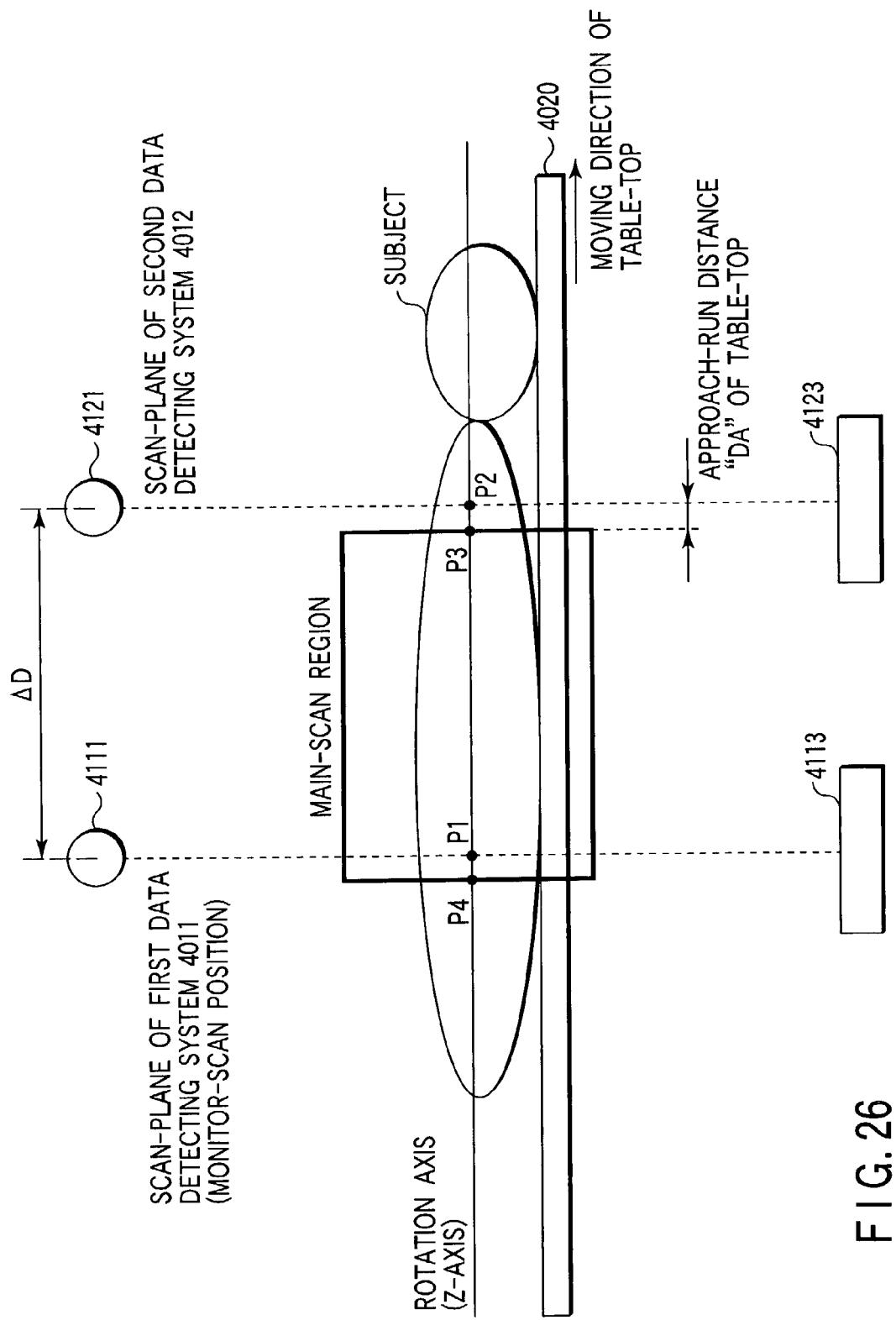
FIG. 26 is a view showing the distance between the first and second data detecting systems in FIG. 24 when a table-top moves in the forward direction.

FIG. 25 shows a procedure for the first operation control. First of all, the operator set scan conditions through the operation console 4026 (S1). The scan conditions are then stored in the memory 4027. As shown in FIG. 26, the scan conditions include a position P1 of a monitor-scan by the first data detecting system 4011, a start position P3 in an imaging region for a main-scan (helical scan) by the second data detecting system 4012, and an end position P4. The scan conditions also include X-ray conditions for a monitor-scan (monitor-scan tube voltage and monitor-scan tube current) and X-ray conditions for a main-scan (main-scan tube voltage and main-scan tube current). Typically, the monitor-scan tube voltage is set to be equal to the main-scan tube voltage so as to exclusively set soft/hard radiation. The monitor-scan tube current is set to be smaller than the main-scan tube current so as to suppress the exposure dose. In addition, the scan conditions include a table-top speed and a scan time (the time required for one rotation) as parameters for determining a helical pitch (the movement distance of the table-top per rotation).

Figure 27:
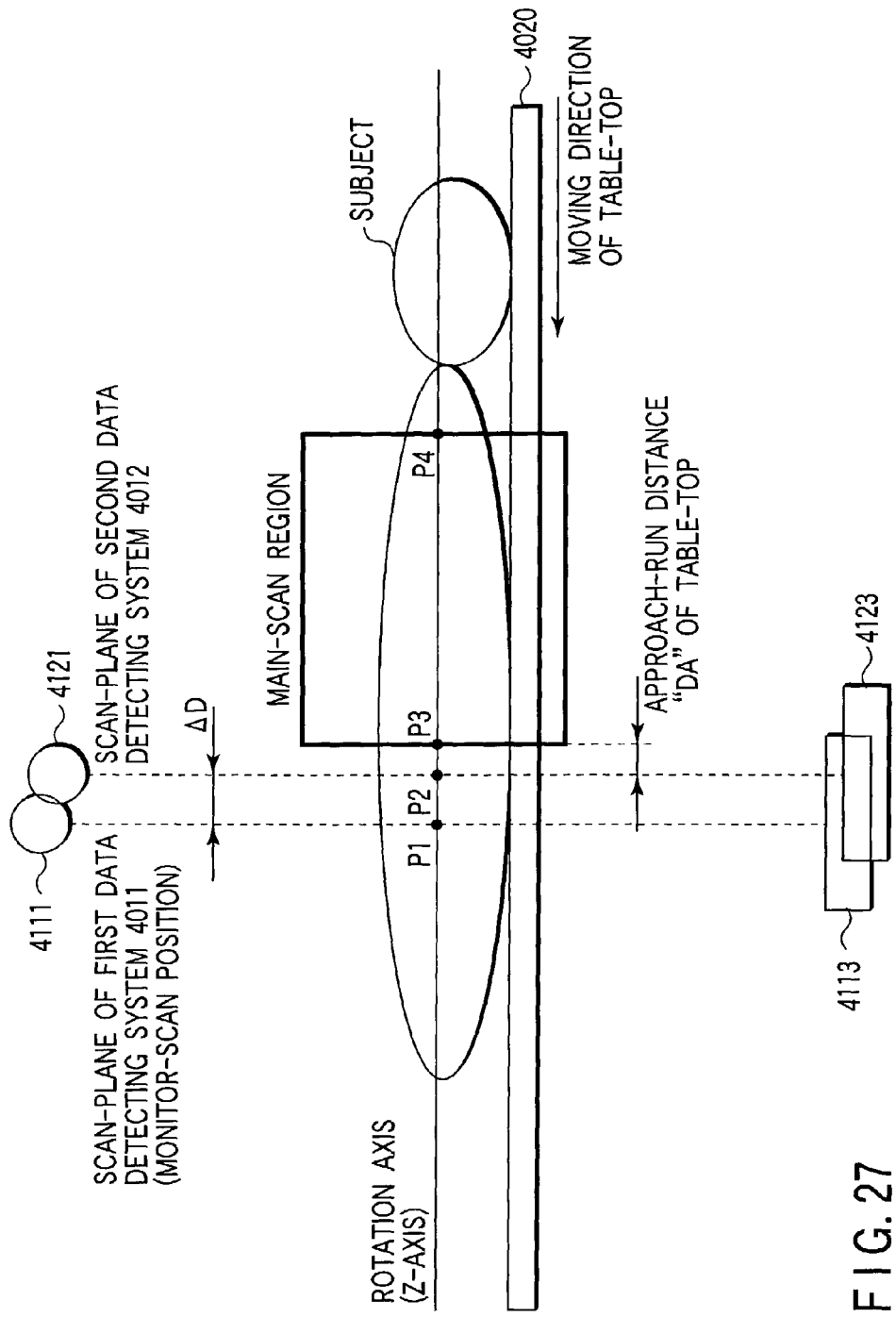
FIG. 27 is a view showing the distance between the first and second data detecting systems in FIG. 24 when the table-top moves in the reverse direction.

When scan conditions are set, the real-prep control unit 4021 calculates a distance ΔD between the scan-planes of the first and second data detecting systems 4011 and 4012 by adding a distance DA required for an approach run through which the table-top reaches a table-top speed in a helical scan from the stop state of the table-top to the distance between the position P1 of the monitor-scan and the start position P3 in the imaging region for the main-scan (S2). When the table-top moves in the reverse direction, the distance ΔD between the scan-planes of the first and second data detecting systems 4011 and 4012 is calculated by subtracting the distance DA required for the approach run through which the table-top reaches the table-top speed in the helical scan from the stop state of the table-top from the distance between the position P1 of the monitor-scan and the start position P3 in the imaging region for the main-scan, as shown in FIG. 27.

The real-prep control unit 4021 controls the Z-shift mechanism driving unit 4019 to separate the scan-plane of the first data detecting system 4011 from the scan-plane of the second data detecting system 4012 by the calculated distance ΔD (S3). The operator then manually operates the table-top 4020 to position a specific region of a subject to be examined to the monitor-scan position P1. At this time, the second data detecting system 4012 is at a standby position P2 located ahead of the start position P3 in the imaging region for the main-scan by the approach run distance DA.

When the above position setting is complete, the real-prep control unit 4021 controls the gantry driving unit 4016 to start rotating the gantry (S4), and sets up the first high voltage generating unit 4014 in accordance with the X-ray conditions for the monitor-scan. Meanwhile, the real-prep control unit 4021 completed the setup of the second high voltage generating unit 4015 in accordance with the X-ray conditions for the main-scan in this stage. More specifically, the real-prep control unit 4021 sets the tube voltage switches of the high voltage generating units 4014 and 4015 in accordance with the monitor-scan tube voltage and main-scan tube voltage, and sets the filament current switches of the high voltage generating units 4014 and 4015 in accordance with the monitor-scan tube current and main-scan tube current. The real-prep control unit 4021 then starts supplying filament heating currents to the first and second X-ray tubes 4111 and 4121 to pre-heat the filaments (S5).

After the above preparatory operation is completed and the rotational speed of the gantry reaches a constant speed, the real-prep control unit 4021 starts a monitor-scan (S6). That is, the real-prep control unit 4021 starts emitting X-rays by supplying an emission trigger to the first high voltage generating unit 4014, and also starts a charge storage/read cycle in the first X-ray detector 4113, signal amplification of the data acquiring unit 4114, analog/digital conversion, and a data read cycle. The real-prep control unit 4021 further controls the image reconstructing unit 4024 to reconstruct an attenuation coefficient distribution as tomographic image data from the projection data obtained by the monitor-scan in real time, and causes the image displaying unit 4025 to display it (S7). This monitor-scan, image reconstruction, and display are consecutively repeated until the processing is stopped in step S12 (to be descried later).

The operator observes this tomographic image, especially the degree of staining of a region of interest (target blood vessel) in the slice, and inputs a pre-trigger for a main-scan through the operation console 4026 at the timing the degree of staining increases to a certain degree (S8).

In response to this pre-trigger, the real-prep control unit 4021 controls the bed driving unit 4017 to start moving the table-top 4020, and also controls the Z-shift mechanism driving unit 4019 to start moving the first data detecting system 4011 at the same speed as that of the movement of the table-top in the same direction (S9). Along with this movement, the start position P3 in the main-scan region gradually approaches the standby position (main-scan position) P2 of the second data detecting system 4012. During this period as well, the monitor-scan, image reconstruction, and display are continued, and the operator observes the tomographic image, especially the degree of staining of the region of interest (target blood vessel) in the slice, thus inputting a trigger for the main-scan through the operation console 4026 at the proper timing (S10).

In response to this trigger for the main-scan, the real-prep control unit 4021 starts the main-scan (helical scan) (S11). That is, the real-prep control unit 4021 starts emitting X-rays by supplying an emission trigger to the second high voltage generating unit 4015, and also starts a charge storage/read cycle in the second X-ray detector 4123, signal amplification by the data acquiring unit 4124, analog/digital conversion, and data read cycle. Note that if no trigger for the main-scan is input when the start position P3 in the main-scan region reaches the standby position P2 of the second data detecting system 4012, the real-prep control unit 4021 automatically starts the main-scan.

This main-scan is continued until the end position P4 in the main-scan region reaches the standby position P2 of the second data detecting system 4012 (S12). When the end position P4 in the main-scan region reaches the standby position P2 of the second data detecting system 4012, the real-prep control unit 4021 stops the monitor-scan together with the main-scan (S13).

As described above, according to this control procedure, since the scan-plane of the first data detecting system 4011 is spaced apart from the scan-plane of the second data detecting system 4012 by the distance ΔD in advance, the wait time for table-top movement can be shortened to the time required for an approach run. In addition, since a monitor-scan is performed by the first data detecting system 4011, and a main-scan is performed by the second data detecting system 4012, the degree of staining can be monitored immediately before the main-scan. Furthermore, since a monitor-scan and main-scan are separately performed by the first and second data detecting systems 4011 and 4012, setups for X-ray emission can be completed in advance in accordance with main-scan conditions. This makes it possible to quickly start the main-scan upon reception of a trigger.

(Second Control Operation)

Figure 28:
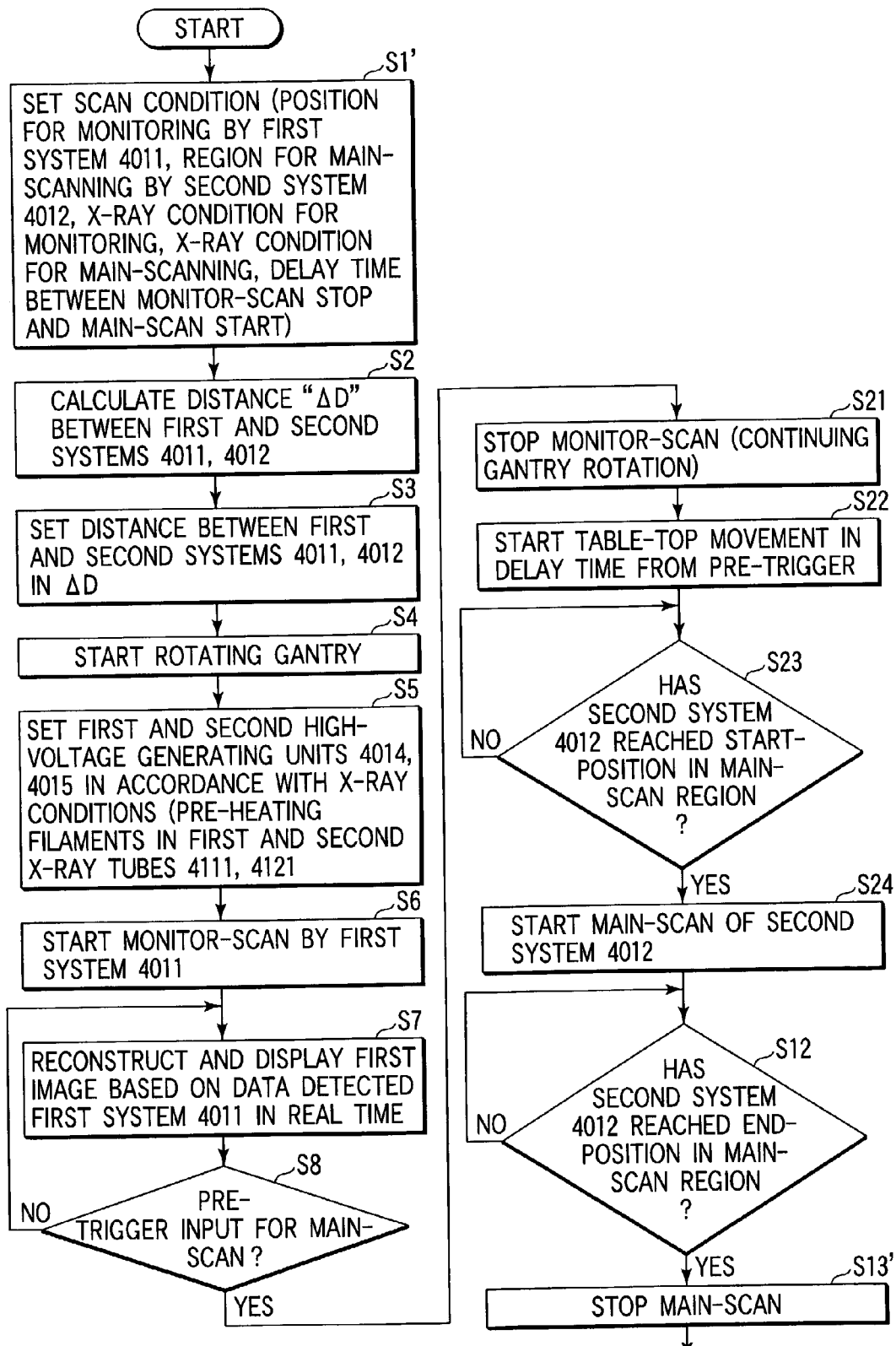
FIG. 28 is a flow chart showing the second control operation by the real-prep control unit in FIG. 24.
Figure 29:
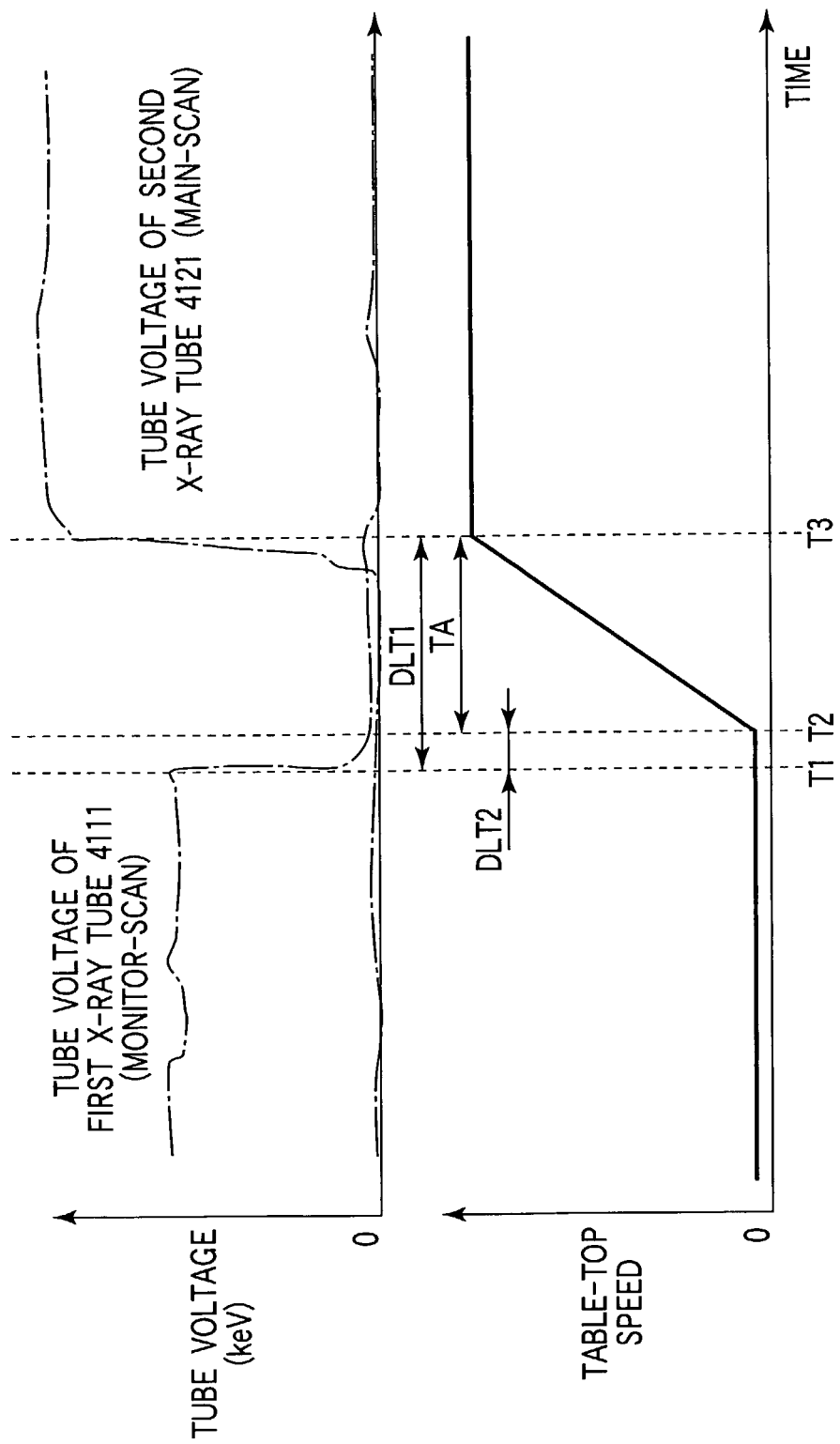
FIG. 29 is a graph showing changes in tube voltage in the first and second X-ray tubes and a change in the moving speed of the table-top moved by a bed driving unit over time in the second control operation in FIG. 28.

In the first control operation, a main-scan trigger is manually input. In the second control operation, however, operation after the input of a pre-trigger is automated. FIG. 28 shows a procedure for the second operation control. The same reference numerals as in FIG. 25 denote the same steps in FIG. 28, and a description thereof will be omitted. FIG. 29 shows changes in tube voltages applied to the first and second X-ray tubes 4111 and 4121 over time and changes in table-top speed over time so as to give an additional explanation to the description of the second control operation.

In this second control operation, as scan conditions, the following are set: a delay time DLT1 between a monitor-scan stop (pre-trigger input) to a main-scan start in addition to the position P1 of a monitor-scan by the first data detecting system 4011, the start position P3 in an imaging region for a main-scan by the second data detecting system 4012, the end position P4, X-ray conditions for the monitor-scan, X-ray conditions for the main-scan, and a table-top speed and scan time which are used to determine a helical pitch (S1'). This delay time DLT1 is set in consideration of the time required for a contrast medium to flow, together with a blood flow, from the position P1 of the monitor-scan by the first data detecting system 4011 to the main-scan start position P3 (which coincides with the scan position P3 of the second data detecting system 4012 at time T3). By setting this delay time DLT1 in advance, the operator can input a pre-trigger when the degree of staining of a tomographic image reaches an optimal degree for the start of the main-scan. That is, there is no need to intentionally delay the timing of inputting a pre-trigger in consideration of the time required for a contrast medium to flow, together with a blood flow, from the monitor-scan position P1 to the start position P3 in an imaging region.

Since operation after pre-trigger input is automated, the real-prep control unit 4021 controls the first X-ray detector 4113 and first data acquiring unit 4114 to stop the monitor-scan in response to the pre-rigger input in step S8 (S21), thus preventing unnecessary exposure to radiation.

The real-prep control unit 4021 then starts moving the table-top 4020 at time T2 after a lapse of only a time DLT2 obtained by subtracting an approach run time Ta from the preset delay time since pre-trigger input time T1 (S22). At time T3 when the table-top 4020 has completed an approach run, the start position P3 in the main-scan region reaches the standby position P2 of the second data detecting system 4012 (S23). At this time, the main-scan is started (S24). Since the monitor-scan has already been stopped, when the end position P4 in the main-scan region reaches the position P2 of the second data detecting system 4012 (S12), the real-prep control unit 4021 stops the main-scan (S13').

As described above, according to the second control operation, in addition to the effects obtained by the first control operation, differences in main-scan start timing and differences among individuals can be eliminated by auto-mating operation after pre-trigger input. This makes it possible to stably perform a main-scan.

(Third Control Operation)

Figure 30:
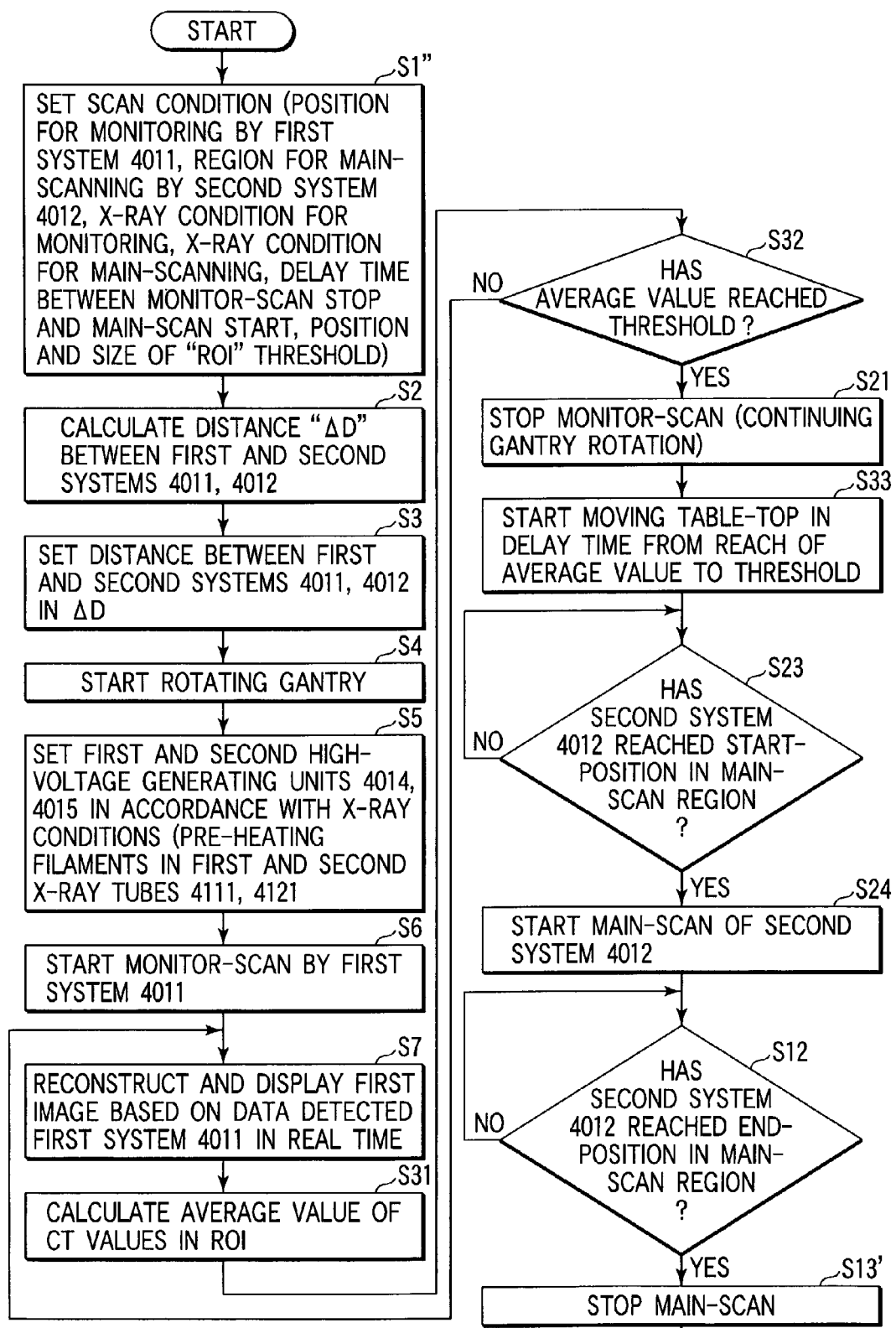
FIG. 30 is a flow chart showing the third control operation by the real-prep control unit in FIG. 24.
Figure 31:
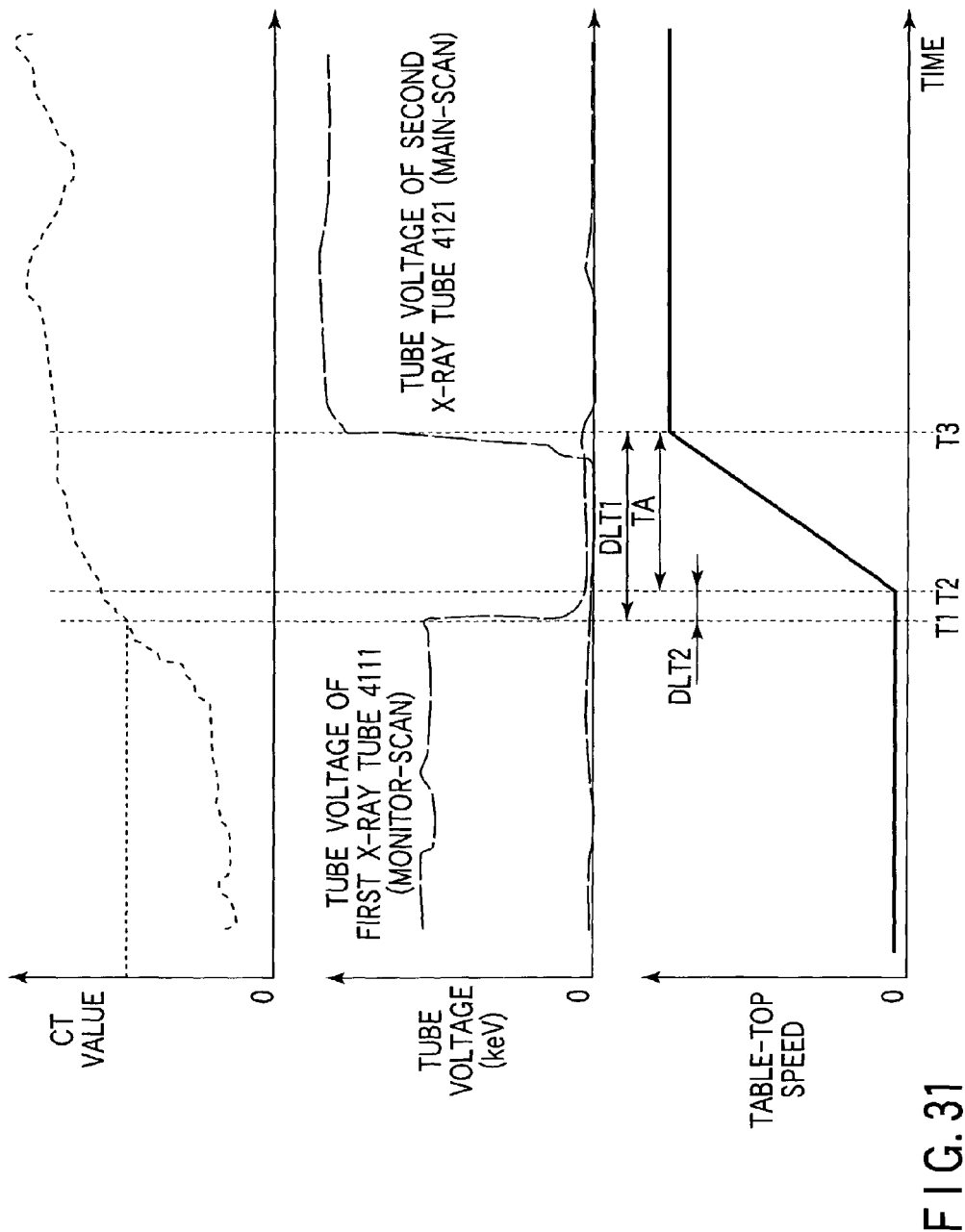
FIG. 31 is a graph showing a change in the average value of CT values of pixels in a region of interest in the first tomographic image obtained by a monitor-scan over time, changes in tube voltage in the first and second X-ray tubes and the bed driving unit over time in the third control operation in FIG. 30.

In the first control operation, a pre-trigger and main-scan trigger are manually input. In the second control operation, a pre-trigger is manually input. In the third control operation, however, pre-trigger input operation is completely automated as well as main-scan trigger input operation. FIG. 30 shows a procedure for the third operation control. The same reference numerals as in FIGS. 25 and 28 denote the same steps in FIG. 30, and a description thereof will be omitted. FIG. 31 shows changes in tube voltages applied to the first and second X-ray tubes 4111 and 4121 over time, changes in table-top speed over time, and changes in the average value of CT values of pixels in a region of interest in the tomographic image obtained by a monitor-scan over time so as to give an additional explanation to the description of the third control operation.

In the third control operation, as scan conditions, the following are set: a region of interest for the automation of pre-trigger input operation and a threshold in addition to the position P1 of a monitor-scan by the first data detecting system 4011, the start position P3 in an imaging region for a main-scan by the second data detecting system 4012, the end position P4, X-ray conditions for the monitor-scan, X-ray conditions for the main-scan, a table-top speed and scan time which are used to determine helical pitch, and the time required for a contrast medium to flow, together with a blood flow, from the position P1 of a monitor-scan by the first data detecting system 4011 to the main-scan start position P3, i.e., the delay time DLT1 between a monitor-scan stop (pre-trigger input) and a main-scan start (S1").

The real-prep control unit 4021 extracts the CT values of a plurality of pixels in the present region of interest from the tomographic image data obtained in step S7, and calculates the average value of the CT values (S31). The real-prep control unit 4021 then compares the calculated CT value (average value) with a preset threshold (S32). If the CT value does not exceed the threshold, the real-prep control unit 4021 determines that the degree of staining at the monitoring position P1 is too low, and repeats CT value extraction, average calculation, and comparison with the threshold with respect to sequentially obtained tomographic image data.

At time T1 when the CT value exceeds the threshold, the real-prep control unit 4021 determines that the degree of staining at the monitoring position P1 is proper, and stops the monitor-scan (S21). As in step S22, the real-prep control unit 4021 starts moving the table-top 4020 at time T2 when the time DLT2 obtained by subtracting the approach run time TA from the preset delay time has elapsed since time T1 when the CT value has exceeded the threshold (S33). At time T3 when the start position P3 in the main-scan region has reached the standby position P2 of the second data detecting system 4012 (S23), the real-prep control unit 4021 starts the main-scan (S24). When the end position P4 in the main-scan region reaches the position P2 of the second data detecting system 4012 (S12), the real-prep control unit 4021 stops the main-scan (S13').

As described above, according to the third control operation, in addition to the effects of the first and second control operations, operation including pre-trigger input operation can be completely automated.

(Fourth Control Operation)

Figure 32A:
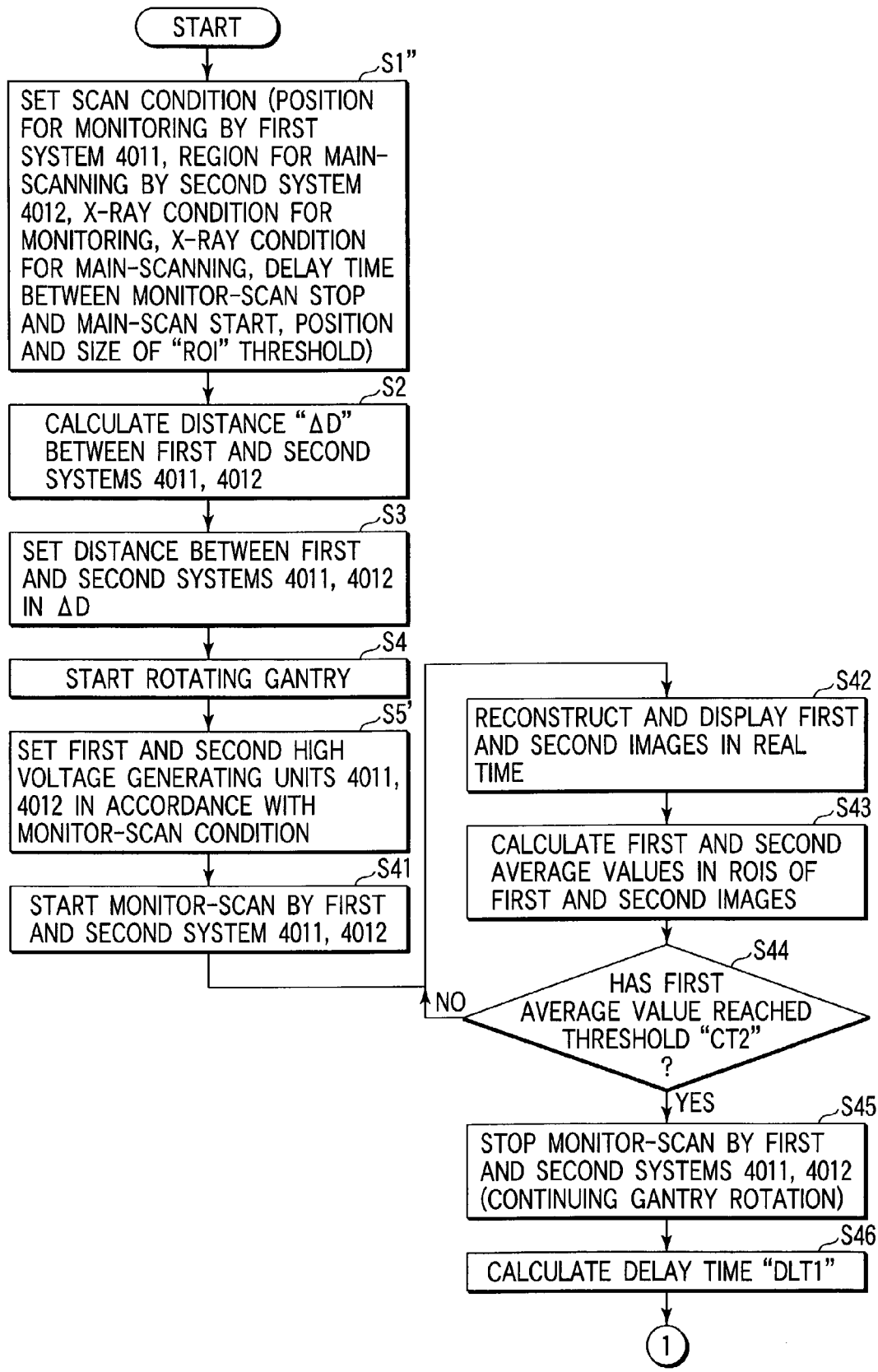
FIG. 32A is a flow chart showing the first half of the fourth control operation by the real-prep control unit in FIG. 24.
Figure 32B:
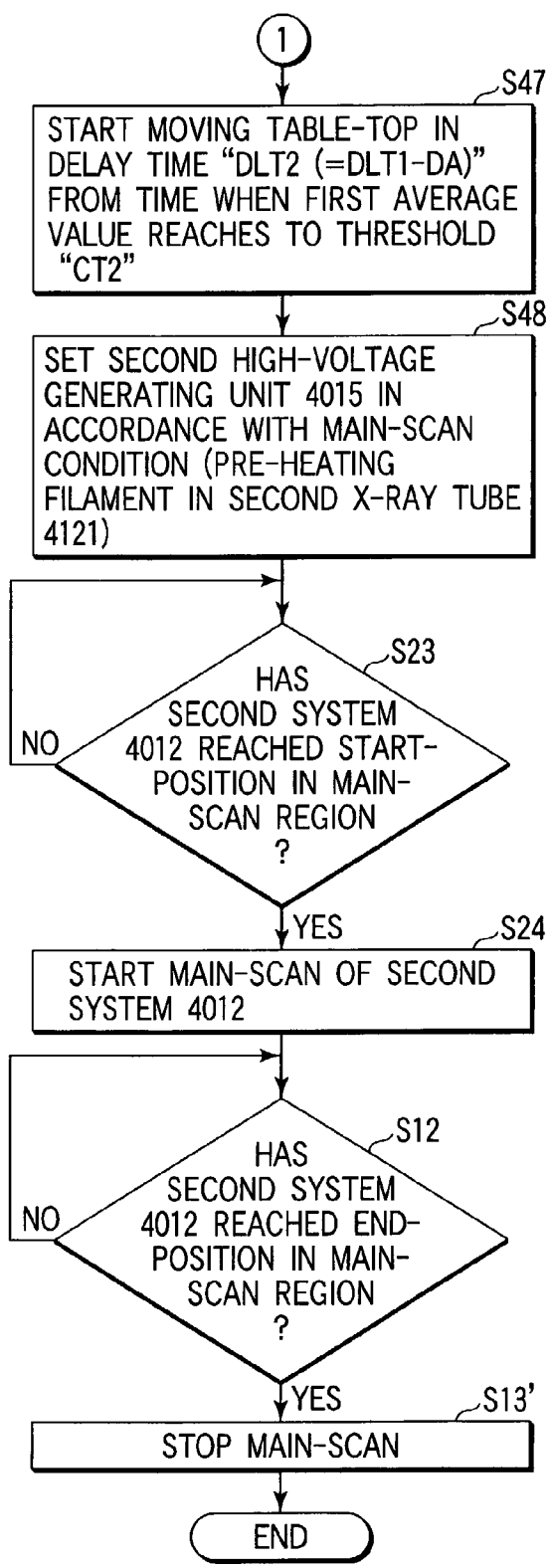
FIG. 32B is a flow chart showing the second half of the fourth control operation by the real-prep control unit in FIG. 24.

In the second and third control operations, the delay time DLT1 from a monitor-scan stop to a main-scan start is set in advance. In the fourth control operation, this delay time DLT1 is obtained by calculation done by the real-prep control unit 4021. FIGS. 32A and 32B show a procedure for the fourth operation control. The same reference numerals as in FIGS. 25, 28, and 30 denote the same steps in FIGS. 32A and 32B, and a description thereof will be omitted. FIG. 33 shows changes in the average value of the CT values of pixels, over time, in a region of interest in the tomographic image data based on the projection data acquired by the first data detecting system 4011 in a monitor-scan and changes in the average value of the CT values of pixels, over time, in the region of interest in the tomographic image data based on the projection data acquired by the second data detecting system 4012 in a monitor-scan so as to give an additional explanation to the description of the fourth control operation.

In this fourth control operation, a monitor-scan is performed not only by the first data detecting system 4011 but also by the second data detecting system 4012. Therefore, in step S5', the second high voltage generating unit 4015 is set up, as well as the first high voltage generating unit 4014, in accordance with X-ray conditions for a monitor-scan.

The real-prep control unit 4021 controls the first and second high voltage generating units 4014 and 4015, first and second X-ray detectors 4113 and 4123, and first and data acquiring units 4114 and 4124 to start monitor-scans in the two data detecting systems 4011 and 4012 (S41). Tomographic image data (first tomographic image data) is reconstructed on the basis of the projection data acquired by the data acquiring unit 4114 by the monitor-scan. Along with this operation, tomographic image data (second tomographic image data) is reconstructed on the basis of the projection data acquired by the data acquiring unit 4124 by the monitor-scan (S42).

The real-prep control unit 4021 extracts the CT values of a plurality of pixels in a preset region of interest from the first tomographic image data obtained in step S42, and calculates the average value (first average value) of the CT values. Along with this operation, the real-prep control unit 4021 extracts the CT values of a plurality of pixels in the region of interest from the second tomographic image data obtained in Step S42, and calculates the average value (second average value) of the CT values (S41). The real-prep control unit 4021 then compares the calculated first average value with a preset threshold CT2 (S44).

If the first average value does not exceed the threshold CT2, the real-prep control unit 4021 determines that the degree of staining at the monitoring position P1 is too low, and repeats first and second average value calculations and comparison between the first average value and the threshold with respect to sequentially obtained tomographic image data. The real-prep control unit 4021 then stores the first and second average values at each time in the memory 4027. When the first average value exceeds the threshold CT2, the real-prep control unit 4021 stops the monitor-scans by the first and second data detecting systems 4011 and 4012 (S45).

The real-prep control unit 4021 then calculates the delay time DLT1 on the basis of changes in the stored first and second average values over time (S46). This delay time DLT1 represents the time required for a contrast medium to flow, together with a blood flow, from the position P1 of the monitor-scan by the first data detecting system 4011 to the main-scan start position P3, i.e., the time difference between the instant at which the degree of staining at the monitor position P1 has reached the specific value (threshold CT2) and the instant at which the degree of staining at the main-scan start position P3 has reached the specific value. Since a change in CT value at the standby position P2 of the second data detecting system 4012 over time almost follows a change in CT value at the monitor position P1 over time, a CT value (CT1) at the standby position P2 of the second data detecting system 4012 at time T12 when the CT value at the monitor position P1 has reached the threshold CT2 is specified, and time T11 when the CT value at the monitor position P1 was the CT1 is extracted from the stored data. This makes it possible to estimate the time width between T11 and T12 as the delay time DLT1.

When the time DLT2 obtained by subtracting the approach run time TA from the calculated delay time DLT1 has elapsed since time T12 when the first average value has exceeded the threshold CT2, the real-prep control unit 4021 starts moving the table-top 4020 (S47), and sets up the second high voltage generating unit 4015 in accordance with X-ray condition for the main-scan (S48).

When the start position P3 in the main-scan region reaches the standby position P2 of the second data detecting system 4012 (P23), the second data detecting system 4012 starts the main-scan (S24). When the end position P4 in the main-scan region reaches the position P2 of the second data detecting system 4012 (S12), the real-prep control unit 4021 stops the main-scan (S13').

As described above, according to the fourth control operation, in addition to the effects of the first, second, and third control operations, the necessity to set the delay time DLT1 from a monitor-scan stop to a main-scan start can be eliminated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   a first data detecting system which includes a first X-ray tube and a first X-ray detector;
   a second data detecting system which includes a second X-ray tube and a second X-ray detector; and
   a reconstructing unit which reconstructs first image data corresponding to a first slice thickness on the basis of an output from the first X-ray detector, and reconstructs second image data corresponding to a second slice thickness smaller than the first slice thickness on the basis of output from the second X-ray detector, further comprising:
   a high voltage generating unit which applies, to the first X-ray tube, a first tube voltage lower than a second tube voltage applied to the second X-ray tube.

2. An apparatus according to claim 1, wherein the first X-ray detector has at least one first detection element line having a plurality of first detection elements which are arrayed, and the second X-ray detector has at least one second detection element line having a plurality of second detection elements which are arrayed.

3. An apparatus according to claim 2, wherein the number of first detection element lines is equal to the number of second detection element lines.

4. An apparatus according to claim 2, wherein the number of first detection element lines is different from the number of second detection element lines.

5. An apparatus according to claim 2, wherein the number of first detection element lines is one.

6. An apparatus according to claim 2, wherein said each first detection element line has a width of an even multiple of a width of said each second detection element line in a slice direction.

7. An apparatus according to claim 6, wherein the first detection element line has a width of 8 mm or 2 mm, and the second detection element line has a width of 0.5 mm.

8. An apparatus according to claim 1, further comprising a Z-shift mechanism which moves the second data detecting system in a slice direction with respect to the first data detecting system.

9. An X-ray computed tomography apparatus comprising:
   a first detecting system which has a first X-ray tube which irradiates a subject to be examined with X-rays at a first irradiation dose, and a first X-ray detector which detects X-rays transmitted through the subject;
   a second detecting system which has a second X-ray tube which irradiates the subject with X-rays at a second irradiation dose higher than first irradiation dose, and a second X-ray detector which detects X-rays transmitted through the subject;
   a moving mechanism configured to move at least one of the first and second data detecting systems in a body axis direction of the subject; and
   a control unit configured to control the moving mechanism so as to set the first data detecting system at a first position and set the second data detecting system at a second position, wherein:

the first detecting system is used for a monitor-scan for monitoring a CT value or contrast medium density, and the second data detecting system is used for a main-scan; and a distance between the first and second positions is determined in consideration of a distance of an approach run of a table-top on which the subject is placed.

10. An apparatus according to claim 9, further comprising a reconstructing unit configured to reconstruct first image data in real time on the basis of an output from the first detector of the first data detecting system.

11. An apparatus according to claim 10, wherein the control unit determines a start timing of the main-scan on the basis of the first image data.

12. An apparatus according to claim 11, wherein the control unit stops irradiating the subject with X-rays from the first X-ray tube before the main-scan.

13. An apparatus according to claim 11, wherein the control unit starts supplying a filament heating current to the second X-ray tube before the main-scan.

14. An apparatus according to claim 11, wherein the control unit compares a pixel value in a region of interest in the first image data or a value derived therefrom with a threshold to determine a start timing of the main-scan.

15. An apparatus according to claim 14, wherein the control unit determines, as a start timing of the main-scan, a point of time when a predetermined period of time has elapsed since a point of time when the pixel value in the region of interest in the first image data or the value derived therefrom has reached the threshold.

16. An apparatus according to claim 9, wherein the control unit starts the main-scan in accordance with an instruction to start the main-scan from an operator.

17. An apparatus according to claim 9, wherein the control unit starts the main-scan at a point of time when a predetermined period of time has elapsed since an instruction to start the main-scan from the operator.

18. An apparatus according to claim 9, wherein the control unit starts supplying a filament heating current to the second X-ray tube before the end of the monitor-scan.

19. An apparatus according to claim 9, wherein the distance between the first and second positions is determined to be a distance obtained by adding or subtracting to or from a distance required for the approach run of the table-top on which the subject is placed from a distance between a position of the monitor-scan and a start position of the main-scan.

* * * * *